United States Patent [19]

Ashley et al.

[11] Patent Number: 5,740,792
[45] Date of Patent: Apr. 21, 1998

[54] INHALER FOR POWDERED MEDICATIONS WITH GEAR-TEETH COUNTER ASSEMBLY

[75] Inventors: Charles R. Ashley, Clinton; Charles M. Huck, Gladstone; Henry R. Sochon, Clifton, all of N.J.; Ken Wilkinson, Round Lake, Ill.

[73] Assignee: Schering Corporation, Kenilworth, N.J.

[21] Appl. No.: 460,604

[22] Filed: Jun. 1, 1995

Related U.S. Application Data

[60] Division of Ser. No. 446,804, filed as PCT/US93/12076, Dec. 16, 1993, which is a continuation-in-part of Ser. No. 992,959, Dec. 18, 1992, abandoned.

[51] Int. Cl.[6] ............................ A61M 15/00; A61M 16/00; B05D 7/14; B05D 83/06
[52] U.S. Cl. ........................... 128/203.15; 128/202.22; 128/205.23; 116/317; 116/299; 222/29; 222/38
[58] Field of Search ..................... 128/200.14, 203.12, 128/203.15, 203.21, 200.23, 202.22, 205.23; 222/29, 36, 38; 239/71, 73; 116/312, 314, 317, 285, 299; 235/1 C, 115, 116

[56] References Cited

U.S. PATENT DOCUMENTS

| | | | |
|---|---|---|---|
| 2,596,370 | 5/1952 | Bush | 235/134 |
| 2,636,469 | 4/1953 | McKay | 116/312 |
| 3,085,745 | 4/1963 | Auberger | 235/94 |
| 3,202,127 | 8/1965 | Struble et al. | 116/299 |
| 3,655,952 | 4/1972 | Johnson et al. | 235/94 R |
| 3,673,979 | 7/1972 | Kunov | 116/285 |
| 3,737,634 | 6/1973 | Gaskill et al. | 116/299 |
| 3,950,939 | 4/1976 | Meisner et al. | 116/299 |

(List continued on next page.)

FOREIGN PATENT DOCUMENTS

| | | |
|---|---|---|
| 0069715 | 1/1983 | European Pat. Off. . |
| 0237507 | 9/1987 | European Pat. Off. . |
| 0451745 | 10/1991 | European Pat. Off. . |
| 0488609 | 6/1992 | European Pat. Off. . |
| 0505321 | 9/1992 | European Pat. Off. . |
| 0518087 | 12/1992 | European Pat. Off. . |
| 2022212 | 7/1970 | France . |
| 2041763 | 9/1980 | United Kingdom . |
| 1290484 | 9/1992 | United Kingdom . |
| 8605991 | 10/1986 | WIPO . |
| 9112040 | 8/1991 | WIPO . |
| 9204928 | 4/1992 | WIPO . |
| 9300123 | 1/1993 | WIPO . |
| 9309832 | 5/1993 | WIPO . |

Primary Examiner—Kimberly L. Asher
Attorney, Agent, or Firm—Eric S. Dicker; Robert A. Franks

[57] ABSTRACT

A powder dispenser includes a powder housing for holding a supply of powdered material to be dispensed, the powder housing including an inhalation conduit provided displaced relation to the powdered material supply; a metering plate including a metered dose hole for holding a metered amount of the powdered material, and positioned below the powdered material supply, the metering plate and the powder housing being relatively rotatable with respect to each other about a common central axis; a counter providing a visual count of the number of doses of the powdered material that have been dispensed or remain to be dispensed in response to the relative rotation, the counter including counter rings providing the visual count, the counter rings being rotatable about the common central axis and having indicia thereon which display the visual count, and an actuating mechanism rotatable about the central axis for incrementally rotating the counter rings in response to the relative rotation; a nozzle for breaking up agglomerates of powdered material from the inhalation conduit to form micronized powdered material, the nozzle including a cavity for changing the direction of flow of the powder from the direction of the inhalation conduit to a second different direction, and a curved wall for substantially continuously changing the direction of flow of the powder in a spiral manner in the second direction in the cavity; and a closure cap covering the powder housing and priming the powder dispenser for use automatically upon removal thereof.

14 Claims, 23 Drawing Sheets

U.S. PATENT DOCUMENTS

| | | | |
|---|---|---|---|
| 3,991,761 | 11/1976 | Cocozza. | |
| 4,069,819 | 1/1978 | Valentini et al.. | |
| 4,188,984 | 2/1980 | Lyall | 141/12 |
| 4,452,239 | 6/1984 | Malem | 128/200.17 |
| 4,524,769 | 6/1985 | Wetterlin | 128/203.15 |
| 4,528,933 | 7/1985 | Allen | 116/312 |
| 4,534,345 | 8/1985 | Wetterlin | 128/203.15 |
| 4,565,302 | 1/1986 | Pfeiffer et al. | 222/38 |
| 4,667,668 | 5/1987 | Wetterlin | 128/203.15 |
| 4,668,218 | 5/1987 | Virtanen | 604/58 |
| 4,805,811 | 2/1989 | Wetterlin | 222/337 |
| 4,817,822 | 4/1989 | Rand et al. | 222/38 |
| 4,841,964 | 6/1989 | Hurka et al. | 128/203.15 |
| 4,860,740 | 8/1989 | Kirk et al. | 128/203.15 |
| 4,907,583 | 3/1990 | Wetterlin et al. | 128/203.15 |
| 5,033,463 | 7/1991 | Cocozza | 128/203.21 |
| 5,243,970 | 9/1993 | Ambrosio et al. | 128/203.15 |
| 5,331,953 | 7/1994 | Andersson et al. | 128/203.15 |
| 5,349,945 | 9/1994 | Wass et al. | 128/203.15 |

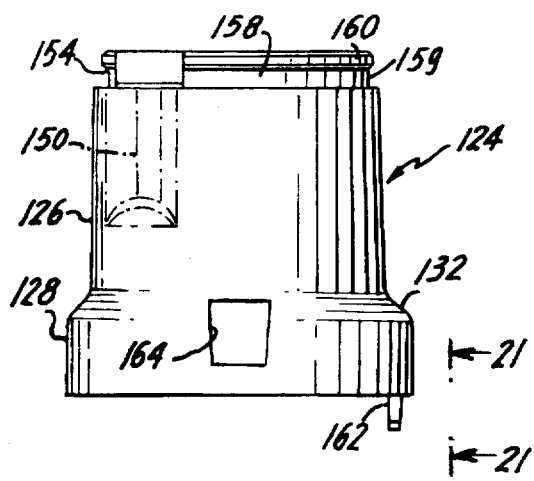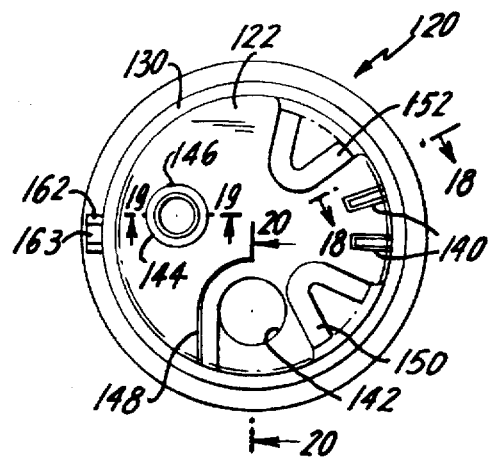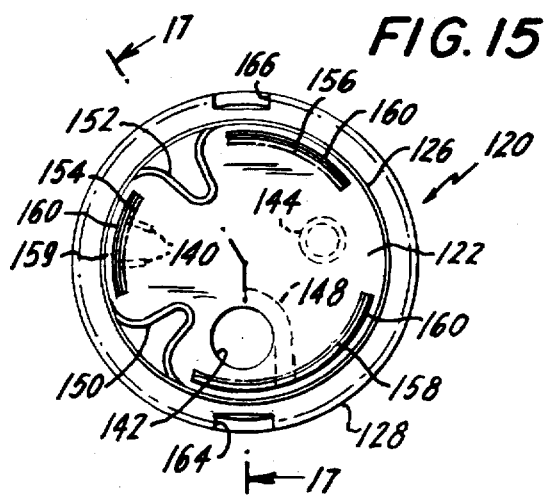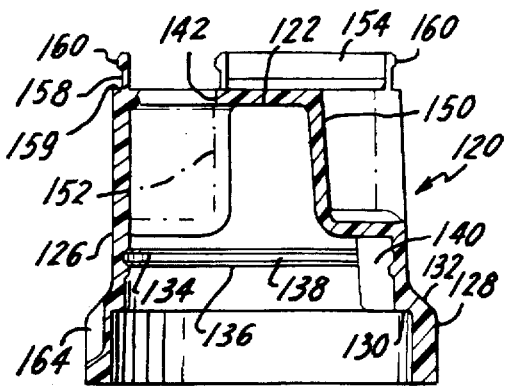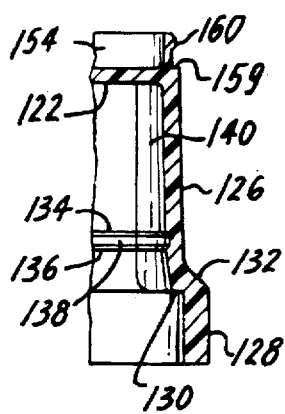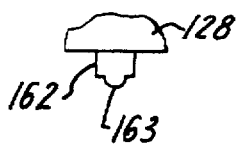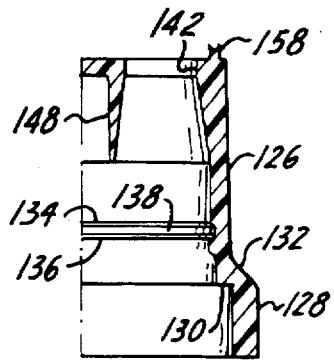

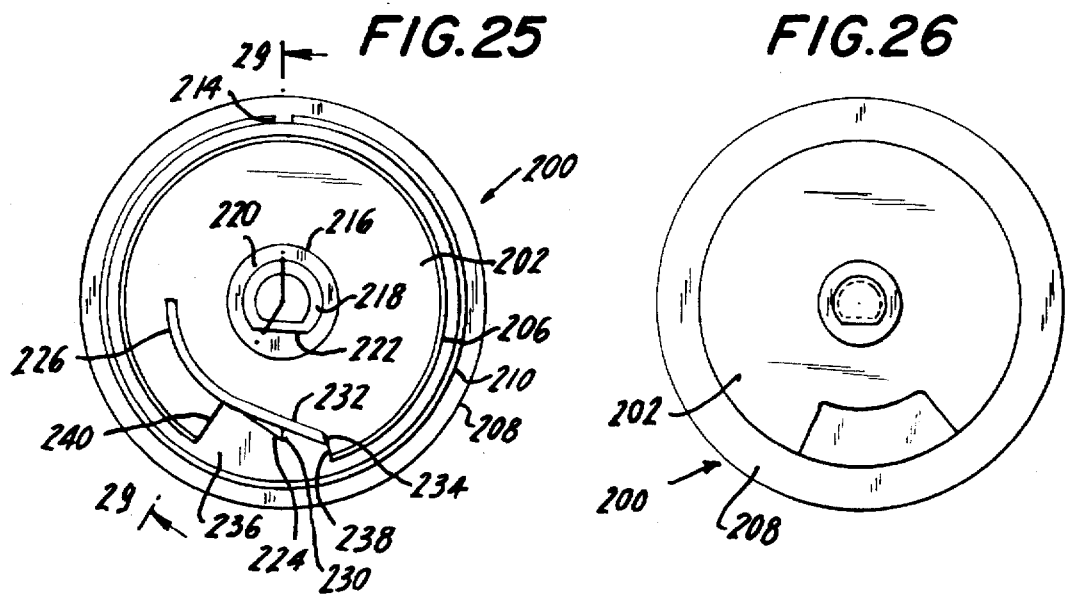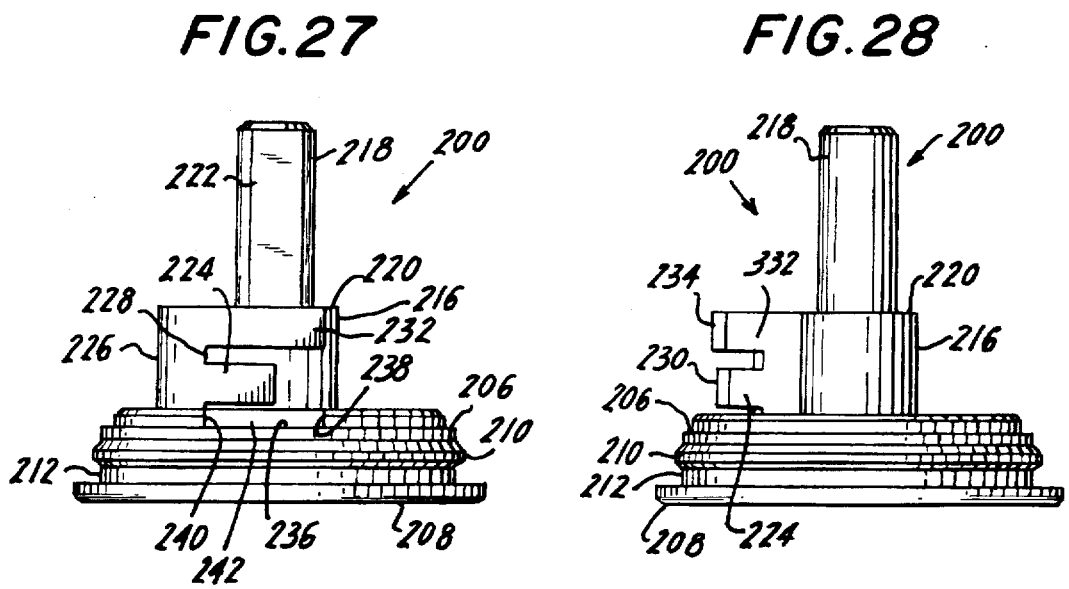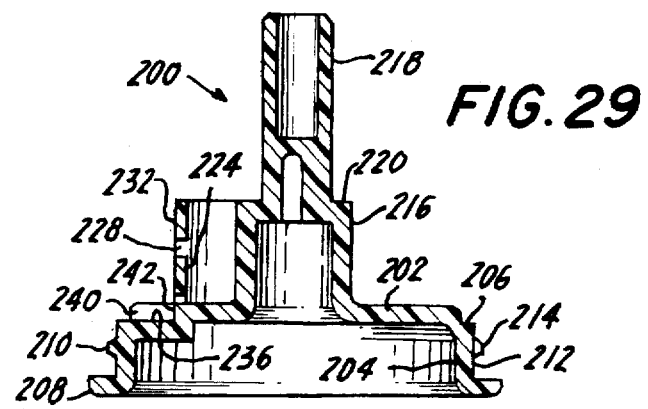

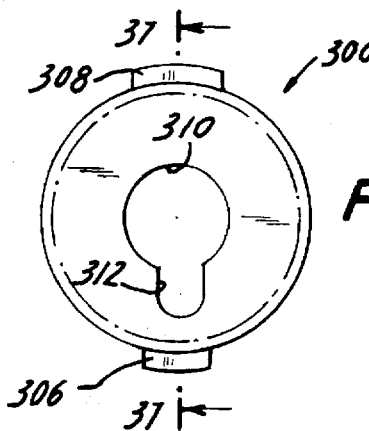
FIG.35
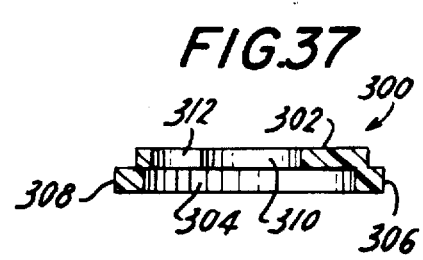
FIG.37
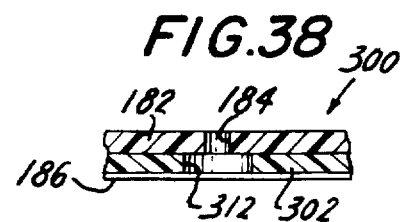
FIG.38
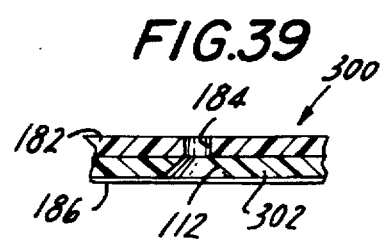
FIG.39
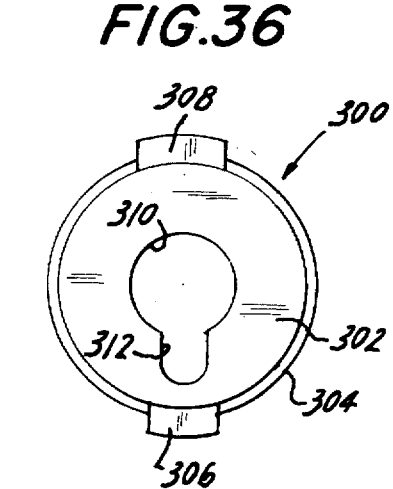
FIG.36
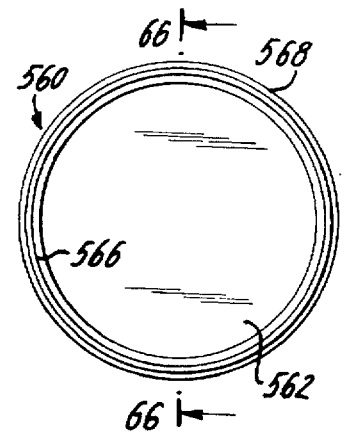
FIG.64
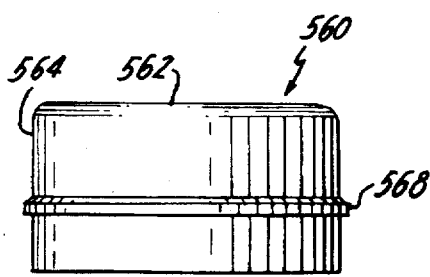
FIG.65
FIG.66

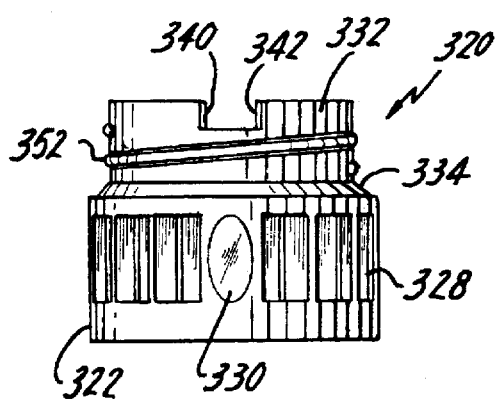
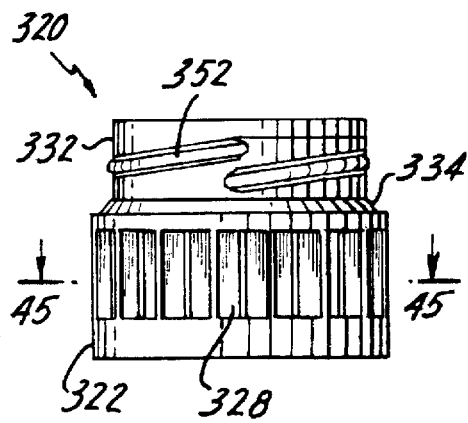
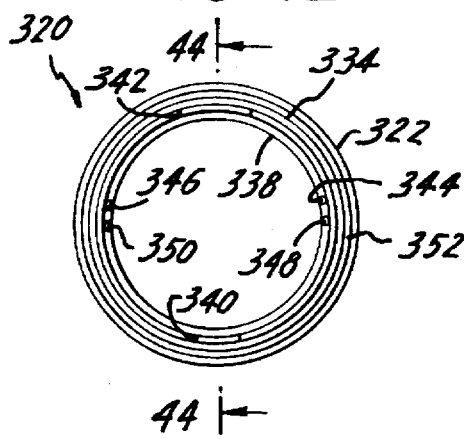
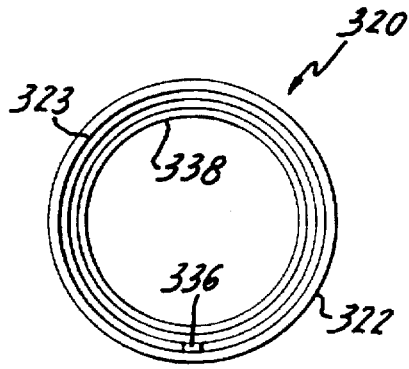
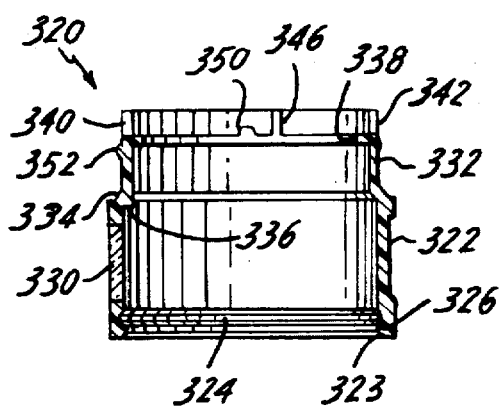
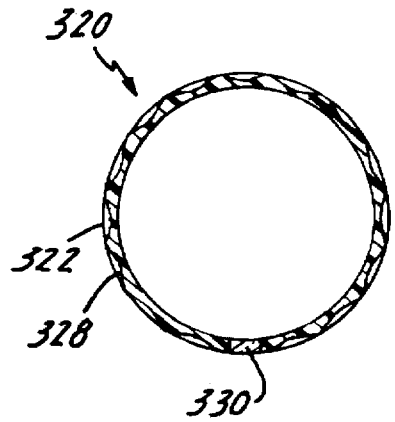

FIG.80
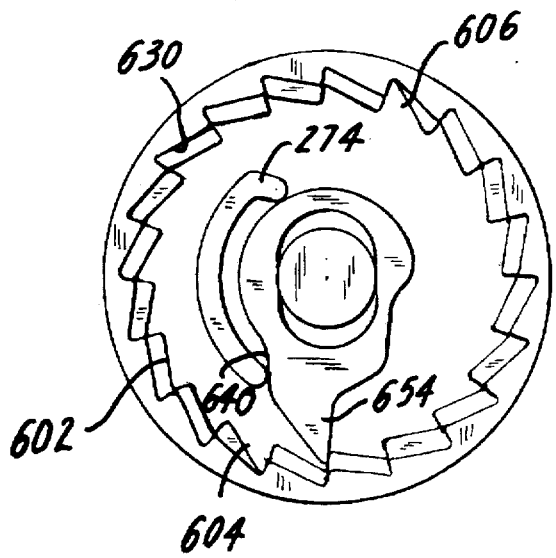
FIG.81
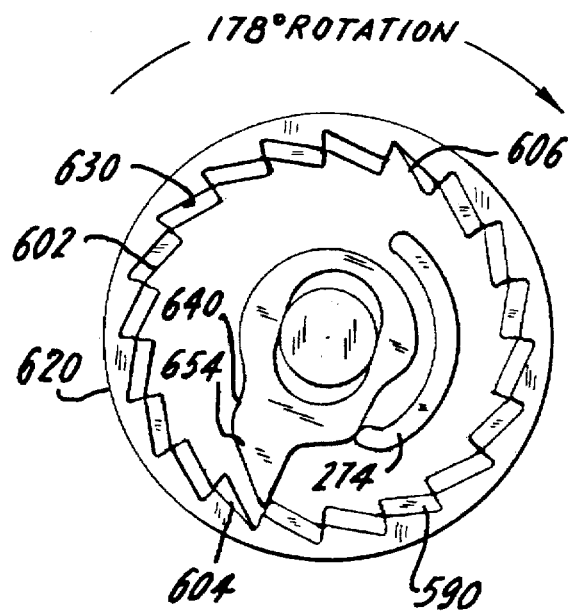
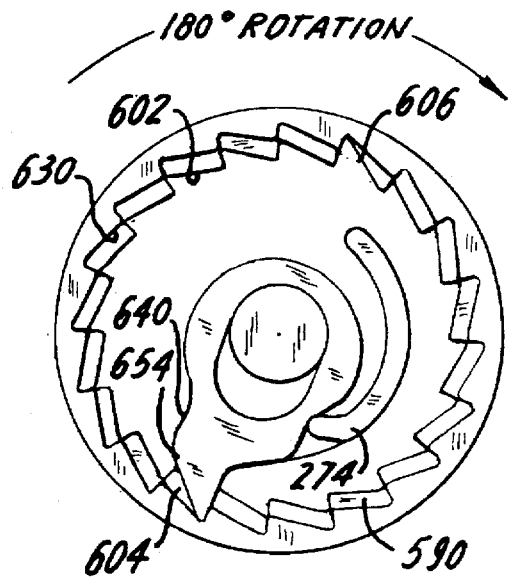
FIG.82

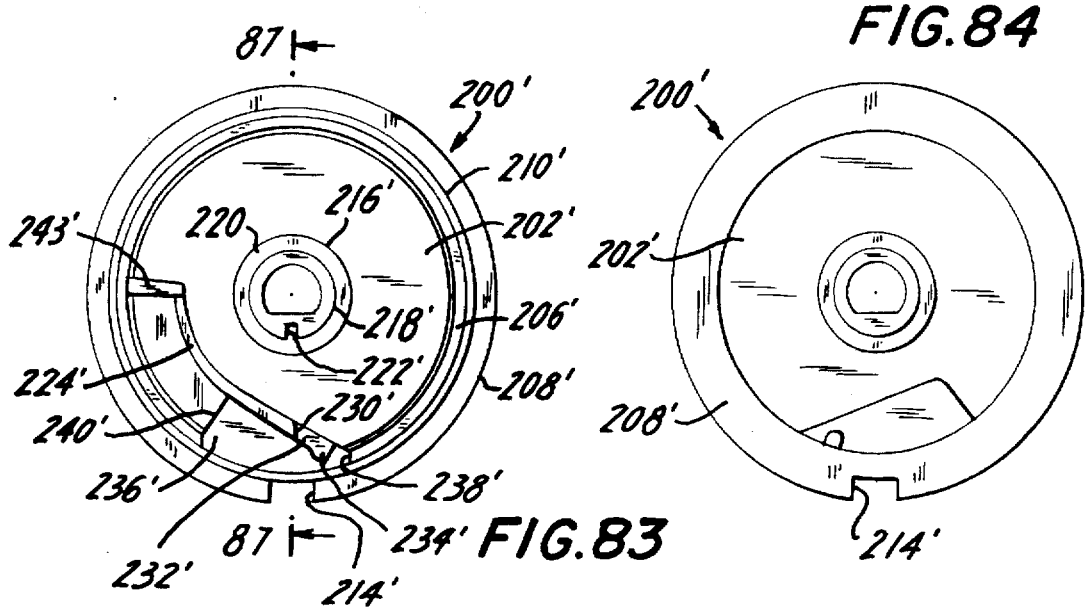
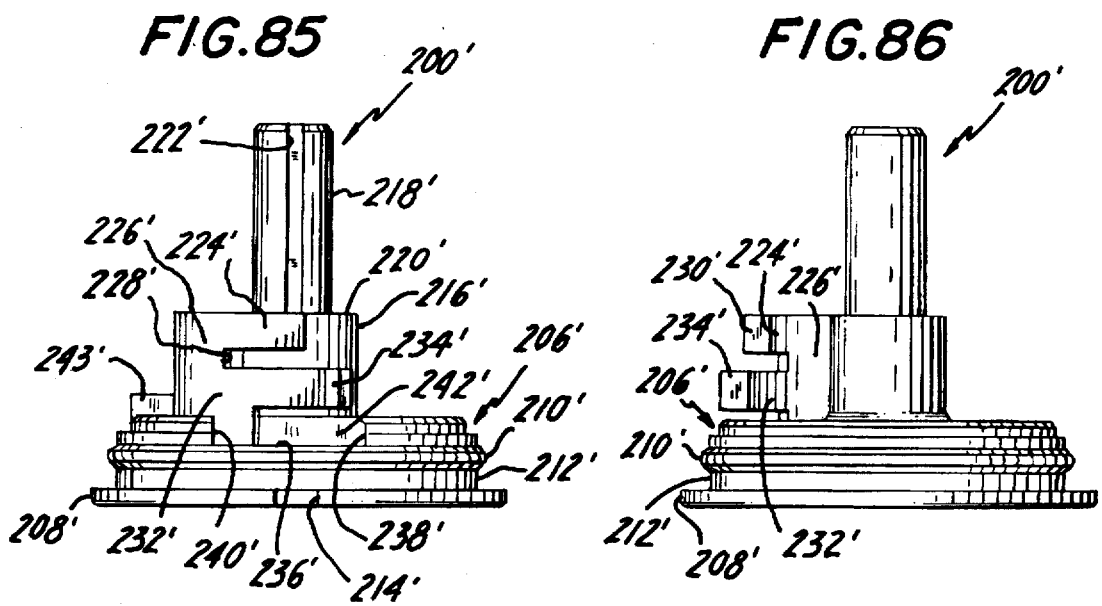
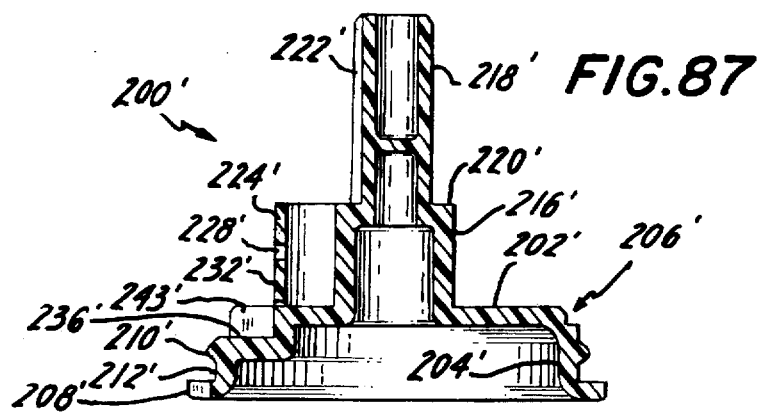

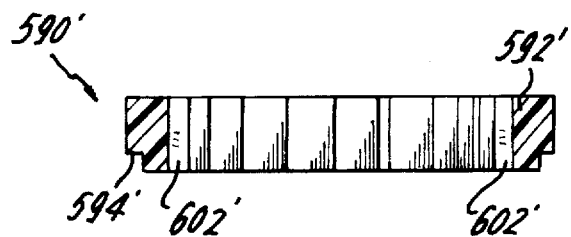
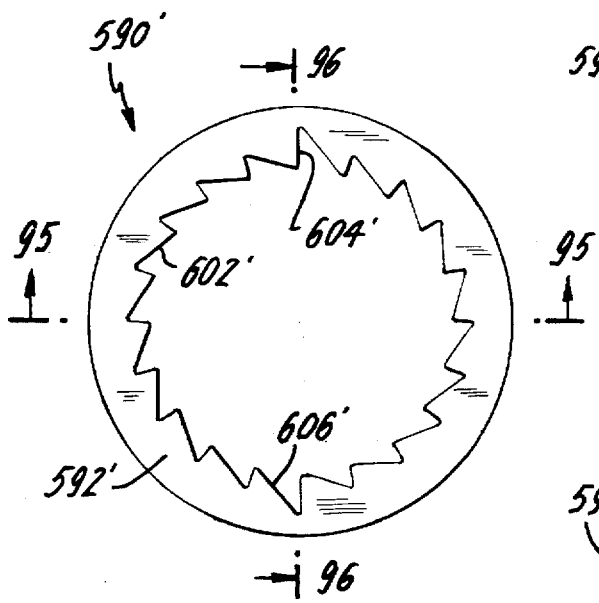
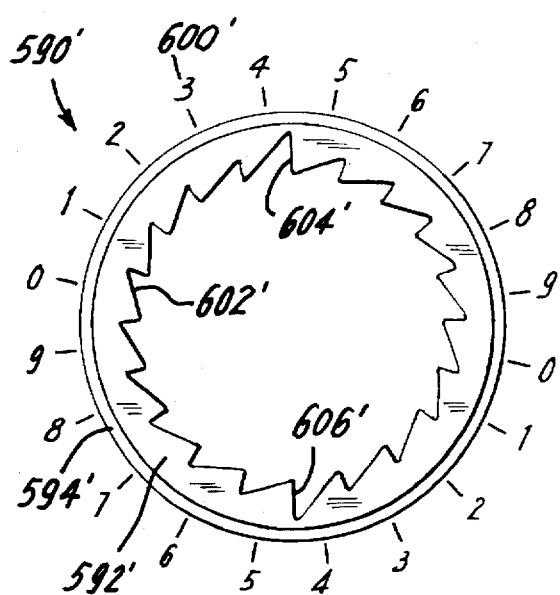
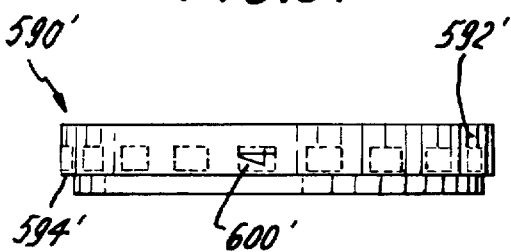

INHALER FOR POWDERED MEDICATIONS WITH GEAR-TEETH COUNTER ASSEMBLY

CROSS-REFERENCE TO RELATED APPLICATIONS

The present application is a divisional of copending Ser. No. 08/446,804 filed on Jun. 1, 1995 as the United States national filing under 35 U.S.C. §371 of PCT International Application No. PCT/US93/12076, filed Dec. 16, 1993, which itself is a continuation-in-part of Ser. No. 07/992,959 filed Dec. 18, 1992 and now abandoned.

INTRODUCTION TO THE INVENTION

The present invention relates generally to powder dispenser assemblies and, more particularly, is directed to a powder dispenser assembly used for inhalation of a metered dose of a powdered medicament.

When delivering medicaments, that is, pharmacologically active compounds, in solid form to the respiratory tract and to the lungs, careful attention to the accuracy of the dosage, which can be smaller than 0.1 milligram, must be made. This is because such medicaments are often quite potent, and the administration of excessive amounts thereof could be harmful to the patient. Further, if the dosage that is delivered is too small, it will not serve its purpose.

It is also necessary that the particles leaving the dispenser assembly be substantially within a particular size range, since particles of the medicament which are too large may not enter the respiratory tract, but instead, will be deposited in the mouth or pharynx and thence enter the digestive tract. As an example, preferred particles can have a diameter of 1 to 5 micrometers.

Various devices have been used in order to dispense a metered dose of powdered medicament, including pressurized aerosol devices, nebulizing devices, pump inhalators and the like. With the current concern over environmental issues, however, aerosol devices, which constitute a large part of the devices now on the market, are less favored. Further, with aerosol devices, the medicament is dissolved or suspended in a liquid propellant mixture, which results in the introduction of unneeded chemical substances into the body and further adds to the complexity of the devices.

In addition to the aforementioned types of dispenser assemblies, powder dispenser assemblies are also known. Studies have shown that there are virtually no significant differences in bronchodilator responses with equivalent amounts of medicinal substances administered either by powder dispensing devices or aerosol devices. Accordingly, there is now an ever-growing demand for powder dispensing devices which can dispense metered doses of powdered medicament. With such devices, the powder is automatically withdrawn during inspiration so there is less need to be concerned with synchronizing release of medication with the exact start of inspiration to insure quality of the product delivery.

U.S. Pat. No. 4,524,769 to Wetterlin, the entire disclosure of which is incorporated herein by reference, describes a dosing unit of the above type that includes a storage chamber for holding the active compound, a perforated membrane rotatably positioned under the storage chamber and a holder for the membrane. Introduction of the active compound into perforations in the perforated membrane is accomplished with elastic, spring-loaded scrapers, mounted in a holder in the storage chamber. With this arrangement, the membrane is movable between a first position where active compound is introduced by the scrapers in part of the area of the perforated membrane, and a second position where the part of the area of the loaded membrane has been inserted into the air conduit in the dosage inhalator. Thus, the active compound contained in the perforations is entrained at inhalation and brought through the nozzle to the respiratory tract and the lungs of the patient.

With this arrangement, a coil spring is used to bias the scrapers into engagement with the perforated membrane. The coil spring is interposed in the storage chamber between the casing and the scraper assembly. Alternatively, it is disclosed that the coil spring can be arranged so that the membrane is pressed against the scrapers, and thereby mounted in the base or maneuvering unit. In addition to the coil spring, Wetterlin uses spring loaded pins beneath the membrane to engage the ratcheted bottom of the membrane in order to provide distinct positions for the perforated membrane when it is advanced by the base or maneuvering unit. See also U.S. Pat. Nos. 4,907,583; 4,534,345; 4,667,668; and 4,805,811; all to Wetterlin.

U.S. Pat. No. 4,668,218 to Virtanen discloses a dispenser substantially identical to the Wetterlin patents, while also providing an indicating assembly which indicates the number of medicament dosages administered. However, Virtanen only provides a single counter ring, which consequently limits the counting capability of doses that are administered. In the case where a dispenser must dispense a large number of doses, for example 200 doses, the arrangement of Virtanen would be totally unacceptable. The limitation in Virtanen is due to the use of a single counter ring that is rotated about an axis orthogonal to the rotatably metering disc and which is rotated one increment for each horizontal rotation of the rotatable metering disc by means of a spiral ridge thereon.

Other disclosures of interest are in U.S. Pat. Nos. 3,085,745 to Auberger; 3,655,952 to Johnson et al; 4,565,302 to Pfeiffer et al; 4,817,822 to Rand et al; and 5,033,463 to Cocozza.

Further, in dry powder inhalers using micronized powder, there can be poor gravitational flow of the powder in micronized form. To improve handling qualities, the powder is processed into small agglomerate spheres having, for example, diameters of approximately one millimeter. During inhalation, the agglomerates are carried through the inhaler flow channels and must be broken up once again into micronized powder before the powder can be deposited in the patient's lungs. This is particularly so since the doses may be very small, on the order of 50 to 100 micrograms, and since particles larger than about 10 microns tend to lodge on surfaces of the mouth and pharynx. The agglomerates are typically much larger than 10 microns.

In known powder dispensers, in order to ensure that the powder is micronized and properly mixed with suction air, helical vanes have been included in the outlet conduit of the mouthpiece. See, for example, U.S. Pat. Nos. 4,907,583 to Wetterlin et al and 5,033,463 to Cocozza. However, such helical vanes do not adequately break up many powder agglomerates.

Still further, with the aforementioned powder dispensers, such as in U.S. Pat. No. 4,805,811 to Wetterlin, it is necessary to separately prime the device for each use, after the cover is removed. This becomes burdensome in practice.

SUMMARY OF THE INVENTION

In accordance with one aspect of the present invention, a counter for a powder dispenser includes a continuous counter ring having counting indicia thereon; an intermittent counter ring adjacent to the continuous counter ring, the intermittent counter ring having counting indicia thereon; display means through which one of the counting indicia from the continuous counter ring and one of the counting indicia from the intermittent counter ring are displayed to indicate a count corresponding to a number of doses of powdered material that have been dispensed or remain to be dispensed; and actuating means for rotating the continuous counter ring one increment each time that a dose of the powdered material is dispensed to display another one of the counting indicia of the continuous counter ring, and for rotating the intermittent counter ring one increment for a predetermined number of rotational increments of the continuous counter ring to display another one of the counting indicia of the intermittent counter ring.

Specifically, the powder dispenser includes a base, and the continuous counter ring and the intermittent counter ring are rotatably mounted relative to the base. The continuous counter ring is rotatably mounted on the base, and the intermittent counter ring is rotatably mounted on the continuous counter ring coaxially with the continuous counter ring. The continuous counter ring has gear teeth therearound, the intermittent counter ring has gear teeth therearound, and the actuating means further includes pawl means, engaging with the gear teeth of the continuous counter ring and the intermittent counter ring, for rotating the continuous counter ring one increment each time that a dose of the powdered material is dispensed to display another one of the counting indicia of the continuous counter ring through the display means, and for rotating the intermittent counter ring one increment every predetermined number of rotational increments of the continuous counter ring to display another one of the counting indicia of the intermittent counter ring through the display means.

The gear teeth of the continuous counter ring are arranged in correspondence with the counting indicia thereon, and the gear teeth of the intermittent counter ring are arranged in correspondence with the counting indicia thereon, on inner surfaces of the respective rings. Further, spring means is provided for biasing the pawl means into engagement with the gear teeth of the continuous counter ring and the intermittent counter ring.

More particularly, the gear teeth of the continuous counter ring include a plurality of successive first gear teeth of a first depth and at least one second gear tooth of a second, greater depth, each the second gear tooth being positioned after every predetermined number of the first gear teeth; and the intermittent counter ring includes a plurality of successive third gear teeth of a depth equal to the depth of each the second gear tooth of the continuous counter ring so that the pawl means engages with successive ones of the first gear teeth during successive dosing operations and engages with one the second gear tooth of the continuous counter ring and one the third gear tooth of the intermittent counter ring after a plurality of the dosing operations.

In addition, detent means is provided for preventing rotation of the continuous counter ring and the intermittent counter ring in a second rotational direction opposite to the first rotational direction in which the pawl means drives the counter rings.

Pawl driver means is provided for incrementally rotating the pawl means, the pawl driver means including a retainer rotatably mounted on the base coaxially with the continuous counter ring and the intermittent counter ring, the retainer including first pawl driver means for engaging with one side of the pawl means to incrementally rotate the pawl means in a first rotational direction at the end of rotation of the retainer in the first rotational direction to cause the pawl means to engage a successive gear tooth of the continuous counter ring, and second pawl driver means for engaging an opposite side of the pawl means to incrementally rotate the pawl means in a second, opposite rotational direction at the end of rotation of the retainer in the second, opposite rotational direction to cause the pawl means to incrementally rotate the continuous counter ring therewith. The first and second pawl driver means are formed as opposite edges of an arcuate pawl driving wall connected with the retainer, wherein the first and second pawl driver means are spaced apart by a distance such that rotation of the retainer by a first arcuate distance causes incremental rotation of the pawl means by a second smaller arcuate distance. Preferably, the first arcuate distance is approximately 180° and the second arcuate distance is approximately 18°.

The above counter is provided in a powder dispenser including powder housing means for holding a supply of powdered material to be dispensed, the powder housing means including an inhalation conduit extending therethrough in displaced relation to the supply of powdered material; and metering plate means for holding a metered amount of the powdered material, the metering plate means including metered dose hole means for holding the metered amount of the powdered material, the metering plate means being positionable below the supply of powdered material, and the metering plate means and the powder housing means being relatively rotatable with respect to each other about a common central axis so that the metered dose hole means is adapted to be in fluid communication selectively with the supply of powdered material or the inhalation conduit. The powder dispenser includes a base having an axially extending retaining post thereon coaxial with the common axis, and the counter rings are rotatably mounted on the base in surrounding relation to the retaining post.

Further, the powder housing means includes holding means for carrying the retainer with the powder housing means during the relative rotation between the metering plate means and the powder housing means about the common central axis. The holding means includes at least one drive slot in the powder housing means and at least one driven ear in the retainer, the at least one drive ear engaging within the at least one drive slot.

In addition, spring means is provided for biasing the metering plate means and the powder housing means toward each other.

In accordance with another aspect of the present invention, a nozzle for breaking up agglomerates of powdered material from an inhalation conduit extending in a first direction in a powder dispenser to form micronized powdered material and for mixing the micronized powdered material with suction air, includes cavity means for changing the direction of flow of the powder from the first direction of the inhalation conduit to a second direction different from the first direction, and swirl means for substantially continuously changing the direction of flow of the powder in the second direction in the cavity means.

The cavity means is defined by a top wall and a skirt connected to a periphery of the top wall in surrounding relation to the swirl means. The top wall includes an opening for changing the direction of flow of the powder from the second direction of the cavity means substantially back to the first direction. Preferably, the top wall has a circular shape and the opening is centrally located in the top wall.

The swirl means includes a curved wall extending from the opening to the skirt, the curved wall extending in a substantially spiral manner. Specifically, the curved wall has a first curved wall section extending partially about the central opening and a second curved wall section extending from one end of the first curved wall section to the skirt, each of the first and second curved wall sections extending essentially along a circular arc, with the radius of the circular arc of the second curved wall section being greater than the radius of the circular arc of the first curved wall section. The curved wall is connected with the top wall.

Chimney means extends from the top wall in surrounding relation to the central opening for changing the direction of flow of the powder from the second direction of the cavity means substantially back to the first direction. The chimney means has a central axis and the inhalation conduit has a central axis parallel to and offset from the central axis of the chimney means.

In accordance with still another aspect of the present invention, a nozzle for breaking up agglomerates of powdered material from an inhalation conduit extending in a first direction in a powder dispenser to form micronized powdered material and for mixing the micronized powdered material with suction air, the nozzle includes an outer wall defining a conduit with a shape substantially that of an inverted tornado.

Specifically, the inverted tornado shape is defined by a continuously changing cross-sectional circular area having a radius which changes exponentially by depth from a lower outer circle of a first radius to an upper circle of a second, smaller radius, and having an origin which moves in a circle that changes with depth. More particularly, the inverted tornado shape is defined by the equation:

$$(x-a)^2+(y-b)^2=c_0+c_1 * e^{-kz},$$

where $a=a_0 * \sine(a_1 * \pi)$, $b=b_0 * \cosine(b_1 * \pi)$, $c_0+c_1$ is the radius of a lowest cross-sectional circular area of the inverted tornado shape, $c_0$ is the radius of an uppermost cross-sectional circular area of the inverted tornado shape, $a_0+a_1$ is the x-coordinate of the lowest cross-sectional circular area, $a_0$ is the x-coordinate of the uppermost cross-sectional circular area, $b_0+b_1$ is the y-coordinate of the lowest cross-sectional circular area, $b_0$ is the x-coordinate of the uppermost cross-sectional circular area, x, y and z are x-, y- and z-coordinates, and k is an exponential coefficient which defines the geometry of a spiral of the inverted tornado shape.

In accordance with yet another aspect of the present invention, a gas permeable retainer means is provided for retaining a dose of the powdered material in the metered dose hole means, the retainer means being positioned below the metered dose hole means. In one embodiment, the retainer means includes a material secured to an underside of the metering plate means and formed by a material selected from the group consisting of a gas-permeable filter, a mesh screen, a porous material and a perforated plate element.

The powder dispenser includes an upper support plate positioned below and in contact with the metering plate means, the upper support plate having an opening larger than the metered dose hole means and in alignment with the metered dose hole means when the metered dose hole means is in alignment with the inhalation conduit, and in an alternative embodiment, the retainer means includes a material secured to an underside of the upper support plate and formed by a material selected from the group consisting of a gas-permeable filter, a mesh screen, a porous material and a perforated plate element.

In addition, rotation limiting means is provided for limiting hi-directional relative rotation between the powder housing means and the metering disc means to a predetermined angle of rotation, for example, 180°.

Lock-out means is also provided for preventing the relative rotation of the powder housing means and the metering plate means after a predetermined number of doses have been dispensed. In this regard, the powder dispenser includes a base on which the metering plate means is non-rotatably mounted and an adapter is non-rotatably mounted on the base. The lock-out means includes a dosage limiter tab on the adapter, and tab means on the counter means for engaging with the dosage limiter tab when the predetermined number of doses have been dispensed.

In accordance with a further aspect of the present invention, the powder dispenser includes closure cap means for covering the powder housing means and for priming the powder dispenser for use, the closure cap means including priming means for rotating the powder housing means such that the inhalation conduit is in communication with the metered dose hole means when the closure cap means is removed from covering relation of the powder housing means, and for rotating the powder housing means such that the inhalation conduit is out of communication with the metered dose hole means and such that the powder supply opening comes into communication with the metered dose hole means as the closure cap means is secured in covering relation to the powder housing means.

Specifically, the adapter includes first helical threads and the closure cap means includes second helical threads for engaging with the first helical threads to threadedly connect the closure cap means on the adapter. The powder housing means includes at least one driving recess and the priming means includes rib means on an inside surface of the closure cap means for engaging with the at least one driving recess to rotate the powder housing means such that the inhalation conduit is in communication with the metered dose hole means when the closure cap means is threadedly removed from the covering relation of the powder housing means and for rotating the powder housing means such that the inhalation conduit is out of communication with the metered dose hole means and such that the powder supply opening comes into communication with the metered dose hole means as the closure cap means is threadedly secured to the adapter means in covering relation to the powder housing means.

The above and other features of the invention will become readily apparent from the following detailed description thereof which is to be read in connection with the accompanying drawings.

BRIEF DESCRIPTION OF THE DRAWINGS

FIG. 14 is a front elevational view of the driving body of the metered powder dose dispenser of FIG. 1;

FIG. 15 is a top plan view of the driving body of FIG. 14;

FIG. 16 is a bottom plan view of the driving body of FIG. 14;

FIG. 17 is a cross-sectional view of the driving body of FIG. 15, taken along line 17—17 thereof;

FIG. 18 is a cross-sectional view of the driving body of FIG. 16, taken along line 18—18 thereof;

FIG. 19 is a cross-sectional view of the driving body of FIG. 16, in inverted position, taken along line 19—19 thereof;

FIG. 20 is a cross-sectional view of the driving body of FIG. 16, taken along line 20—20 thereof;

FIG. 21 is a side elevational view showing the counter stop tab of the driving body of FIG. 14, viewed along line 21—21 thereof;

FIG. 25 is a top plan view of the base of the metered powder dose dispenser of FIG. 1;

FIG. 26 is a bottom plan view of the base of FIG. 25;

FIG. 27 is a front elevational view of the base of FIG. 25;

FIG. 28 is a side elevational view of the base of FIG. 25;

FIG. 29 is a cross-sectional view of the base of FIG. 25, taken along line 29—29 thereof;

FIG. 35 is a top plan view of the support plate of the metered powder dose dispenser of FIG. 1;

FIG. 36 is a bottom plan view of the support plate of FIG. 35;

FIG. 37 is a cross-sectional view of the support plate of FIG. 35, taken along line 37—37 thereof;

FIG. 38 is a cross-sectional view of a portion of the metering dose plate, support plate and powder retainer according to an alternative embodiment of the present invention;

FIG. 39 is a cross-sectional view of a portion of the metering dose plate, support plate and powder retainer according to another alternative embodiment of the present invention;

FIG. 40 is a front elevational view of the adapter of the metered powder dose dispenser of FIG. 1; FIG. 41 is a side elevational view of the adapter of FIG. 40;

FIG. 42 is a top plan view of the adapter of FIG. 40;

FIG. 43 is a bottom plan view of the adapter of FIG. 40;

FIG. 44 is a cross-sectional view of the adapter of FIG. 42, taken along line 44—44 thereof;

FIG. 45 is a cross-sectional view of the adapter of FIG. 41, taken along line 45—45 thereof;

FIG. 64 is a bottom plan view of a desiccant holder of the metered powder dose dispenser of FIG. 1;

FIG. 65 is a side elevational view of the desiccant holder of FIG. 64;

FIG. 66 is a cross-sectional view of the desiccant holder of FIG. 64, taken along line 66—66 thereof;

FIG. 80 is a schematic view showing the relationship between the arcuate pawl driving wall of the lower spring retainer, the continuous counter ring, the intermittent counter ring and the pawl assembly in the stored position;

FIG. 81 is a schematic view similar to FIG. 80 when the arcuate pawl driving wall has been rotated 178° toward the inhalation position; and FIG. 82 is a schematic view similar to FIG. 80 in the inhalation position.

FIG. 83 is a top plan view of the base according to another embodiment of the metered powder dose dispenser of FIG. 1;

FIG. 84 is a bottom plan view of the base of FIG. 83;

FIG. 85 is a front elevational view of the base of FIG. 83;

FIG. 86 is a side elevational view of the base of FIG. 83;

FIG. 87 is a cross-sectional view of the base of FIG. 83, taken along line 87—87 thereof;

FIG. 93 is a top plan view of the continuous counter ring according to another embodiment of the metered powder dose dispenser of FIG. 1;

FIG. 94 is a bottom plan view of the continuous counter ring of FIG. 93;

FIG. 95 is a cross-sectional view of the continuous counter ring of FIG. 93, taken along line 95—95 thereof;

FIG. 96 is a cross-sectional view of the continuous counter ring of FIG. 93, taken along line 96—96 thereof;

FIG. 97 is a side elevational view of the continuous counter ring of FIG. 93;

DETAILED DESCRIPTION OF SPECIFIC EMBODIMENTS

Figure 2:
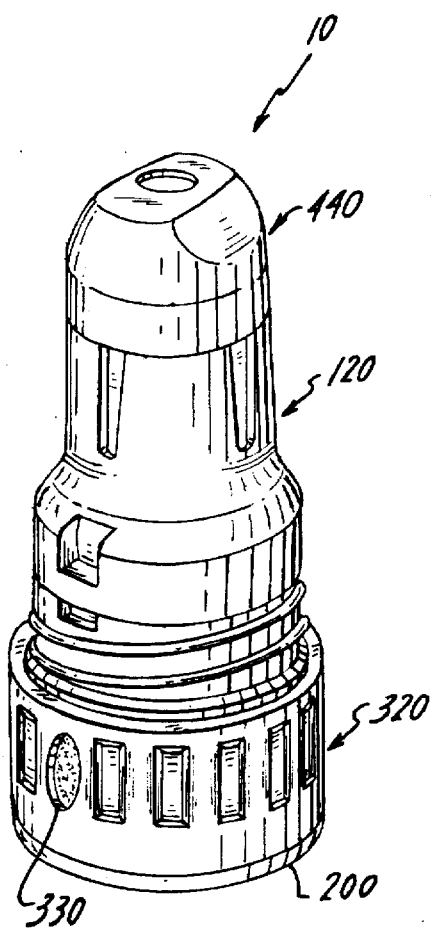
FIG. 2 is a perspective view of the metered powder dose dispenser of FIG. 1, with the closure cap removed.
Figure 1:
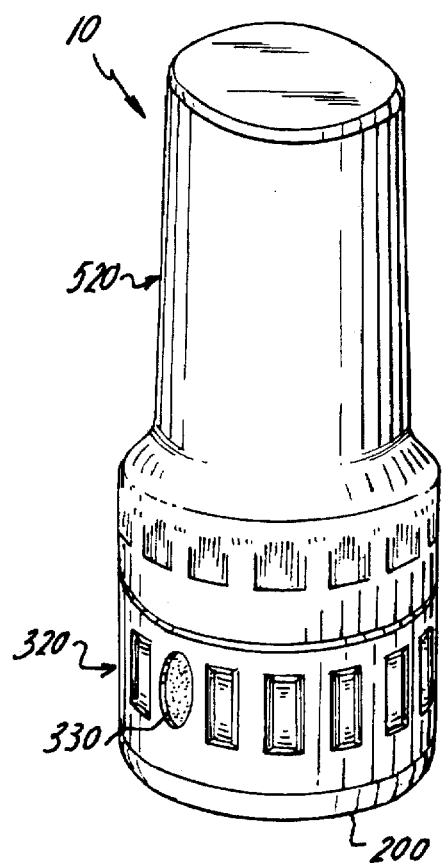
FIG. 1 is a perspective view of a metered powder dose dispenser according to the present invention.
Figure 3:
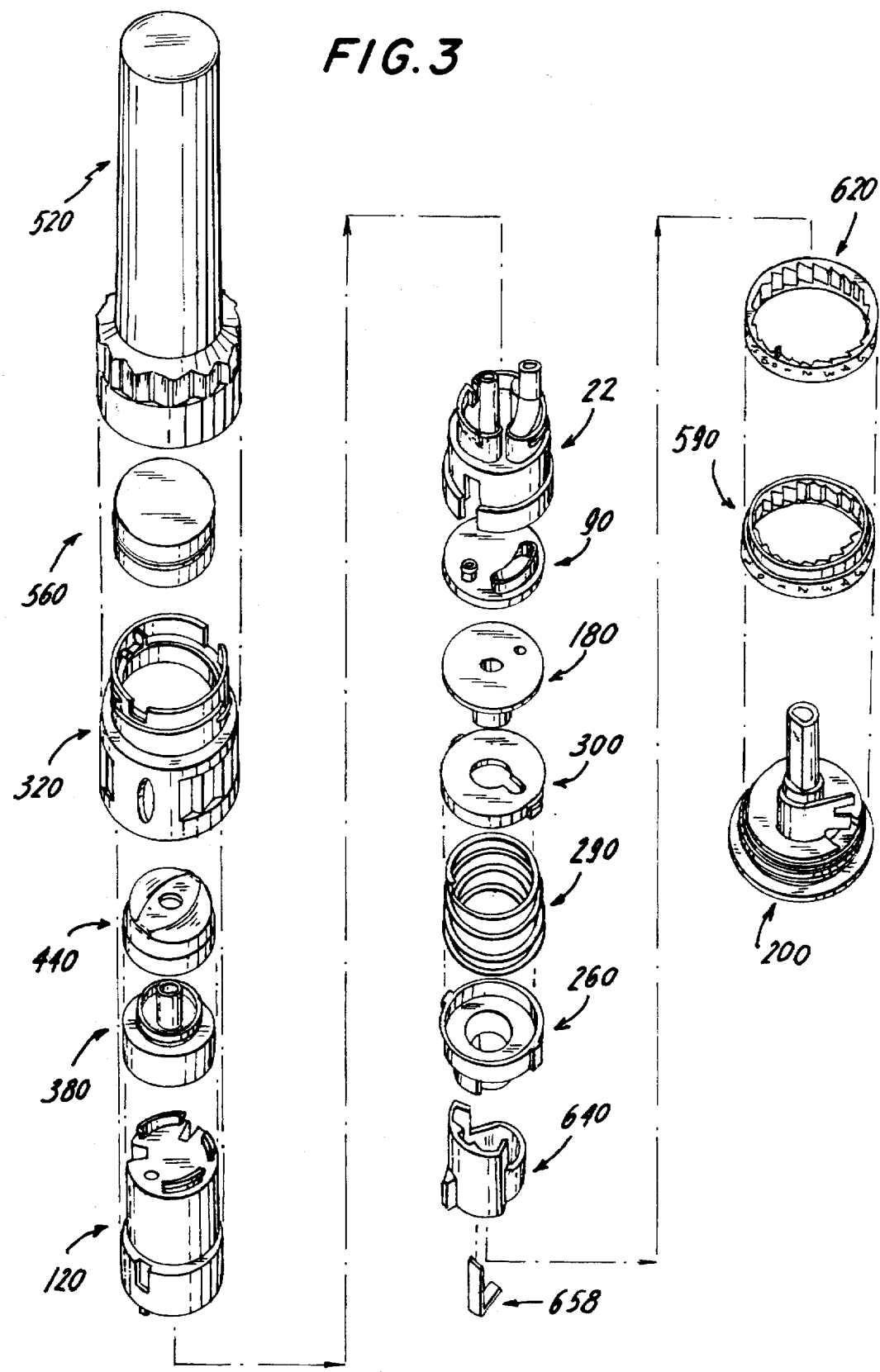
FIG. 3 is an exploded perspective view of the metered powder dose dispenser of FIG. 1.

Referring to the drawings in detail, and initially to FIGS. 1–4 thereof, a metered powder dose dispenser 10 according to the present invention includes a powder housing 20 for holding a supply of powdered material to be dispensed, and for supplying metered doses of the powder to a user.

Powder housing 20 is comprised of a reservoir body 22, a reservoir plug 90 and a driving body 120, each being formed as a single molded plastic piece.

Referring to FIGS. 3–8, reservoir body 22 includes a circular top wall 24 having an annular skirt 26 extending downwardly from the periphery of circular top wall 24. Annular skirt 26 includes an upper annular skirt section 28 with its upper end extending downwardly from the periphery of circular top wall 24, and a lower annular skirt section 30 extending downwardly from the lower end of upper annular skirt section 28. Lower annular skirt section 30 has an inner and outer diameter greater than the inner and outer diameters, respectively, of upper annular skirt section 28. Accordingly, an outer annular shoulder 32 is formed at the upper end of lower annular skirt section 30.

Diametrically opposite, axially extending drive slots 34 and 36 are formed in annular skirt 26, each extending for a different circumferential angular extent about annular skirt 26. For example, drive slot 34 is shown to extend along a 30° arc circumferentially of annular skirt 26, while drive slot 36 is shown to extend along a 40° arc circumferentially of annular skirt 26. Of course, the present invention is not limited to these particular angles. Drive slots 34 and 36 are open at their lower ends 38 and 40, respectively, and extend upwardly entirely through lower annular skirt portion 30 and partially through upper annular skirt portion 28. Thus, drive slots 34 and 36 have closed upper ends which define seating edges 42 and 44.

Powder housing 28 includes an arcuate manifold 46 formed on the upper surface of circular top wall 24, at a peripheral position offset from the center thereof. Manifold 46 includes an arcuate chamber 47 extending circumferentially for an arcuate length of approximately 140° about a peripheral portion of circular top wall 24 and which is defined by a surrounding chamber wall 48. Specifically, chamber wall 48 is formed by a lower chamber wall portion 50 extending upwardly from circular top wall 24 and an upper chamber wall portion 52 extending upwardly from the upper end of lower chamber wall portion 50. The shapes of wall portions 50 and 52 are substantially identical, but with the inner dimensions of upper wall portion 52 being less than the inner dimensions of lower wall portion 50. As a result, a shoulder 54 is formed at the lower end of upper chamber wall portion 52.

Circular top wall 24 includes an opening 55 of the same shape and dimensions as lower chamber wall portion 50 of manifold 46 and in alignment with the lower end of lower chamber wall portion 50. The upper end of manifold 46, and particularly upper chamber wall portion 52, is closed by a manifold top wall 56 which is angled downwardly from the center thereof and which has an opening 58 at the center thereof.

A powder supply conduit 60 is formed on manifold top wall 52 at the center thereof in alignment with opening 58. The upper end of powder supply conduit 60 is open. Powder supply conduit 60 is normally filled with powder 62 for inhalation. As used herein, the terms "powdered medicaments" and "powder" include micronized powder, spheronized powder, micro-encapsulated powder, powder agglomerates and the like, and are used interchangeably with these terms herein.

A frusto-conical inhalation venturi conduit 64 is also formed on circular top wall 24 substantially parallel to powder supply conduit 60 and axially offset from the central axis of circular top wall 24. The center axis of powder supply conduit 60 and the center axis of venturi conduit 64 lie on a circle having a center coincident with the center of circular top wall 24, so as to be positioned at a peripheral portion of circular top wall 24, the center axes of conduits 60 and 64 being spaced apart along such a circle by an angle of approximately 105°.

Specifically, venturi conduit 64 is formed by a lower venturi conduit section 66 and an upper venturi conduit section 68 axially aligned therewith, each reducing in inner diameter from a lower end thereof to an upper end thereof. The upper end of upper venturi conduit section 68 is open, and upper venturi conduit section 68 has a smaller diameter than lower venturi conduit section 66 so that an inner annular shoulder 70 is formed at the lower edge of upper venturi conduit section 68. Circular top wall 24 includes a further opening 72 of the same shape and dimensions as the lower end of lower venturi conduit section 66 and in alignment therewith.

A peripheral securing wall 74 extends generally about a circular arc on a peripheral portion of circular top wall 24, in surrounding relation to lower chamber wall portion 50 and lower venturi conduit section 66. A gap 76 is provided in securing wall 74 at a position opposite conduits 60 and 64, and two parallel, spaced apart, radially extending tabs 78 extend inwardly from opposite ends of securing wall 74 at gap 76. Further, a radially extending annular lip 80 extends outwardly from the upper end of securing wall 74.

As will be understood from the description hereinafter, it is necessary that the lower surface of circular top wall 24 be as smooth as possible, that is, with very few undulations therein. However, this is difficult to achieve when molding reservoir body 22 as a single piece. Therefore, to overcome this problem, a reservoir plug 90 is provided, as shown in FIGS. 3, 4 and 9–13.

Figure 4:
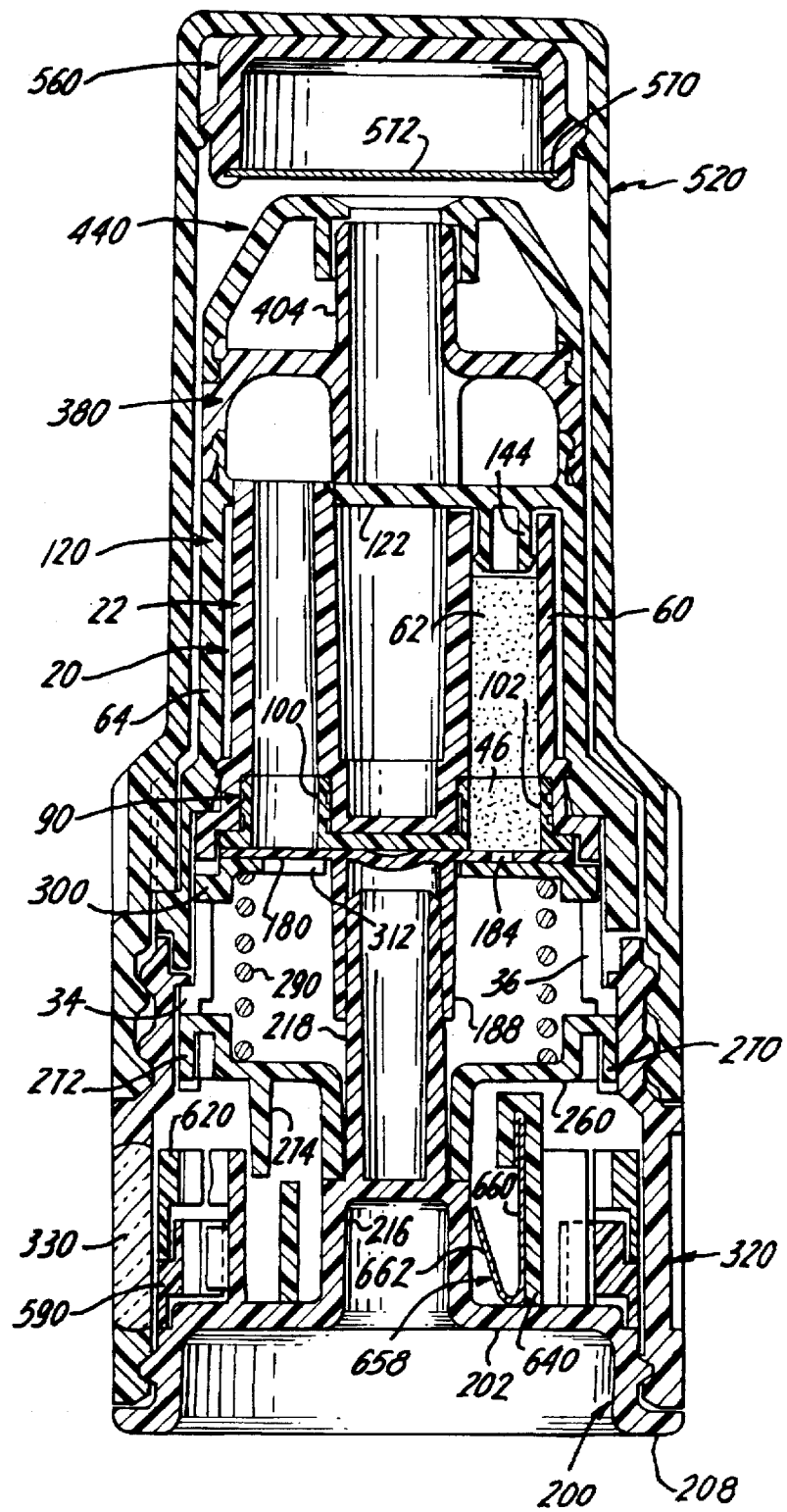
FIG. 4 is a longitudinal cross-sectional view of the metered powder dose dispenser of FIG. 1.
Figure 5:
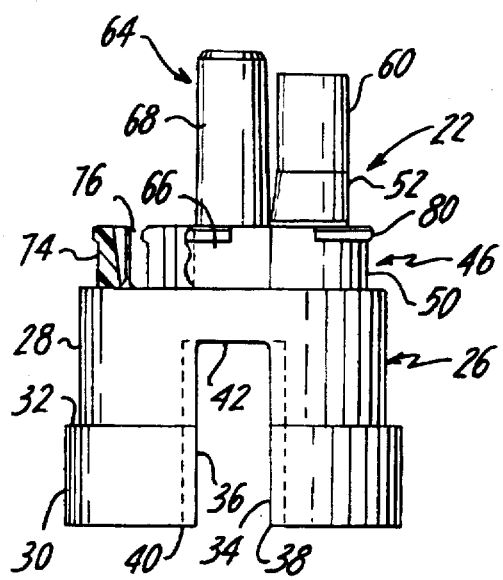
FIG. 5 is a front elevational view, partially in cross-section, of the reservoir body of the metered powder dose dispenser of FIG. 1.
Figure 7:
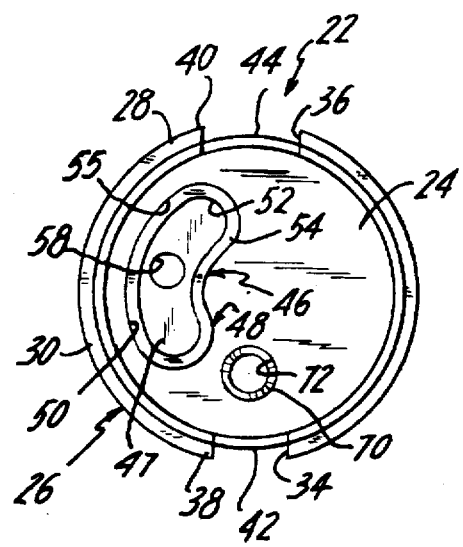
FIG. 7 is a bottom plan view of the reservoir body of FIG. 5.
Figure 6:
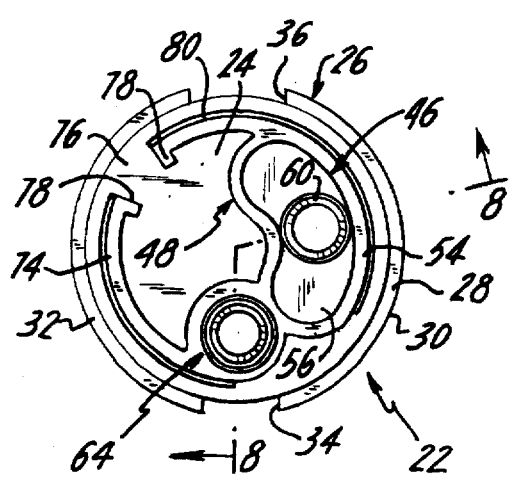
FIG. 6 is a top plan view of the reservoir body of FIG. 5.
Figure 8:
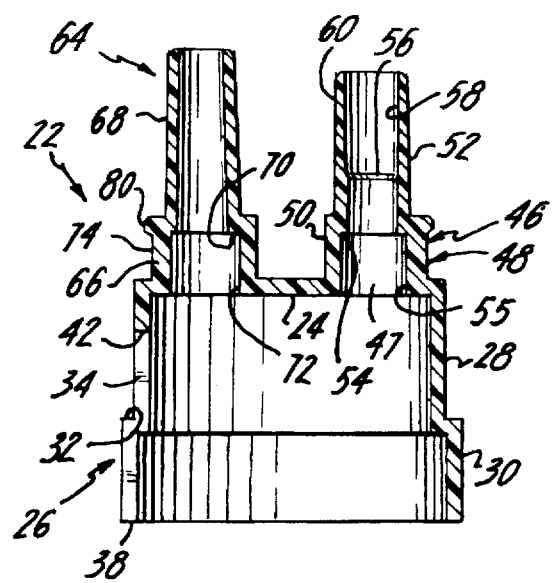
FIG. 8 is a cross-sectional view of the reservoir body of FIG. 6, taken along line 8—8 thereof.
Figure 9:
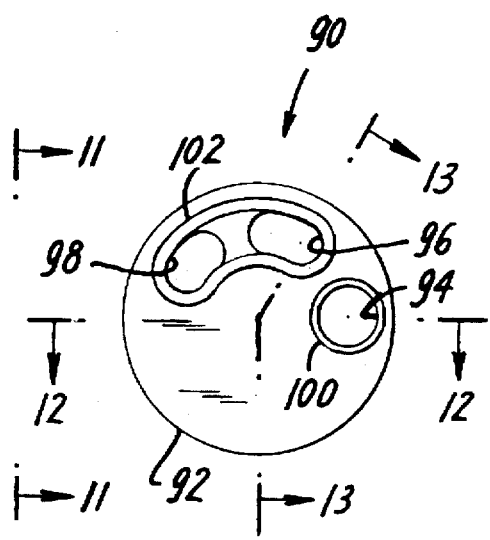
FIG. 9 is a top plan view of the reservoir plug of the metered powder dose dispenser of FIG. 1.
Figure 10:
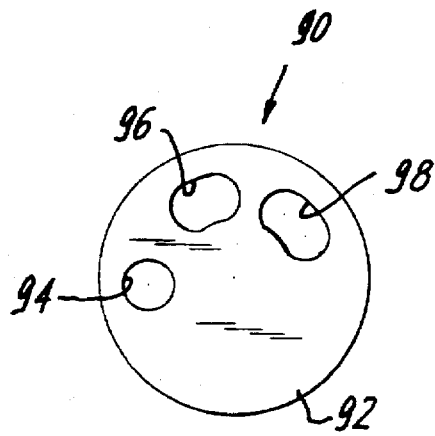
FIG. 10 is a bottom plan view of the reservoir plug of FIG. 9.
Figure 11:
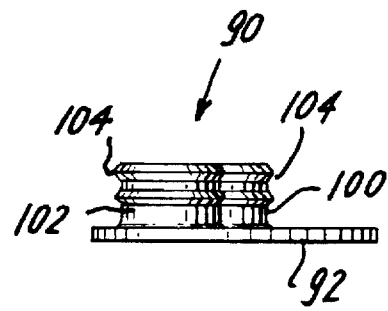
FIG. 11 is a side elevational view of the reservoir plug of FIG. 9, viewed from line 11—11 thereof.

Specifically, reservoir plug 90 includes a thin circular plate 92 which can be molded, because of the thinness of plate 92, to have a very smooth lower surface with no undulations. The outer diameter of circular plate 92 is substantially equal to the inner diameter of upper annular skirt portion 28 so that reservoir plug 90 can be fit therein, as shown in FIG. 4. In such condition, the lower surface of circular plate 92 effectively is flush with seating edges 42 and 44 of drive slots 34 and 36.

Circular plate 92 has a circular hole 94, a first substantially oval hole 96 and a second substantially oval hole 98, all having centers extending along an imaginary circle centered at the center of plate 92.

A circular plug conduit 100 is formed on the upper surface of circular plate 92 in surrounding relation to circular hole 94. Conduit 100 is open at its upper and lower ends and has an outside diameter and a height substantially equal to the inside diameter and height, respectively, of lower venturi conduit section 66 and an inside diameter equal to the inside diameter of upper venturi conduit section 68. Thus, when reservoir plug 90 is inserted within upper annular skirt section 28, plug conduit 100 fits snugly within lower venturi conduit section 66 and the inner surface of plug conduit 100 forms a smooth continuation of the inner surface of upper venturi conduit section 68. In such condition, the upper edge of plug conduit 100 abuts against annular shoulder 70 so that no gap is formed between plug conduit 100 and upper venturi conduit section 68.

An arcuate plug conduit 102 is formed on the upper surface of circular plate 92 in surrounding relation to first and second substantially oval holes 96 and 98. Plug conduit 102 has the same shape as lower chamber wall portion 50 of manifold 46. Plug conduit 102 is open at its upper and lower ends and has an outside shape and dimensions substantially equal to the inside shape and dimensions, respectively, of lower chamber wall portion 50, inside shape and dimensions equal to the inside shape and dimensions of upper chamber wall portion 52, and a height equal to the height of lower chamber wall portion 50. Thus, when reservoir plug 90 is inserted within upper annular skirt section 28, plug conduit 102 fits snugly within lower chamber wall portion 50 and the inner surface of plug conduit 102 forms a smooth continuation of the inner surface of upper chamber wall portion 52. In such condition, the upper edge of plug conduit 102 abuts against shoulder 54 so that no gap is formed between plug conduit 102 and upper chamber wall portion 52.

Figure 12:
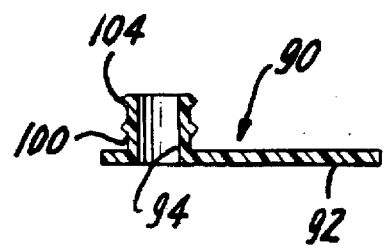
FIG. 12 is a cross-sectional view of the reservoir plug of FIG. 9, taken along line 12—12 thereof.
Figure 13:
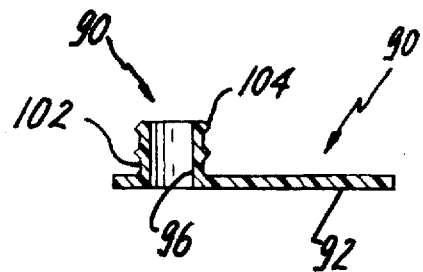
FIG. 13 is a cross-sectional view of the reservoir plug of FIG. 9, taken along line 13—13 thereof.
Figure 30:
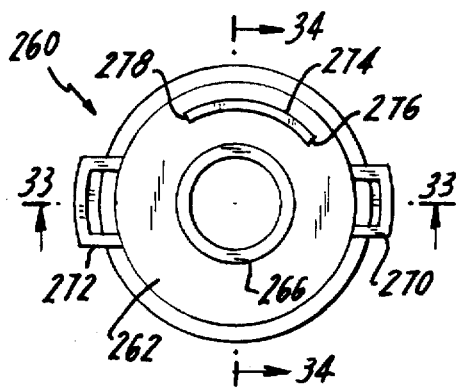
FIG. 30 is a bottom plan view of the lower spring retainer of the metered powder dose dispenser of FIG. 1.
Figure 33:
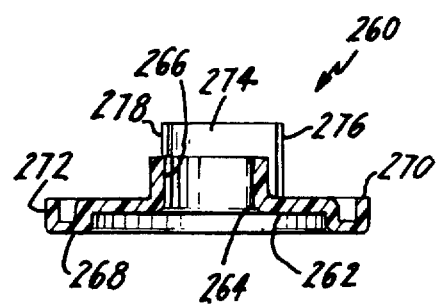
FIG. 33 is a cross-sectional view of the lower spring retainer of FIG. 30, taken along line 33—33 thereof.
Figure 31:
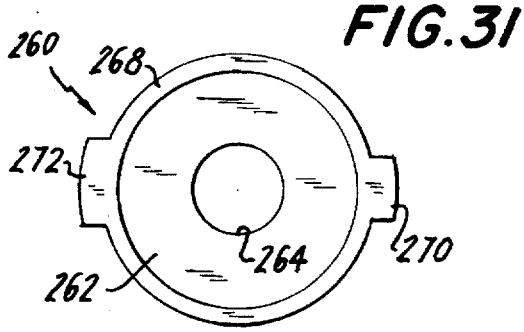
FIG. 31 is a top plan view of the lower spring retainer of FIG. 30.
Figure 34:
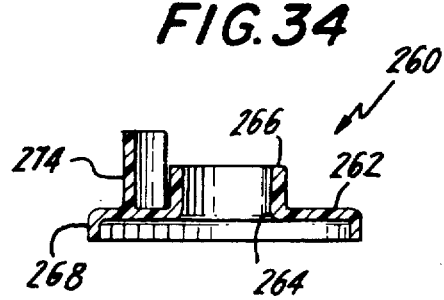
FIG. 34 is a cross-sectional view of the lower spring retainer of FIG. 30, taken along line 34—34 thereof.
Figure 32:
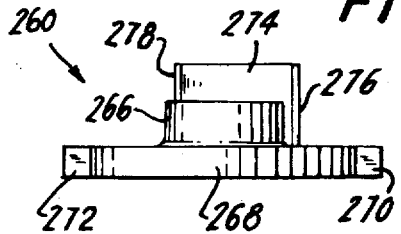
FIG. 32 is a side elevational view of the lower spring retainer of FIG. 30.
Figure 23:
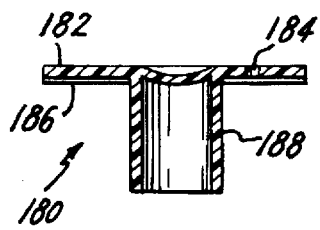
FIG. 23 is a cross-sectional view of the metering dose plate of FIG. 22, taken along line 23—23 thereof.
Figure 22:
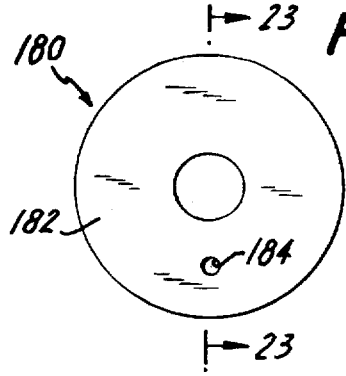
FIG. 22 is a top plan view of the metering dose plate of the metered powder dose dispenser of FIG. 1.
Figure 24:
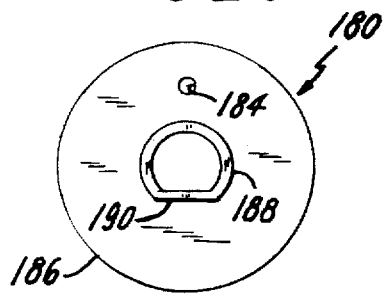
FIG. 24 is a bottom plan view of the metering dose plate of FIG. 22.
Figure 46:
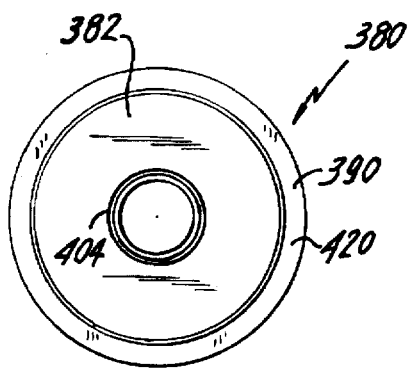
FIG. 46 is a top plan view of the swirl nozzle of the metered powder dose dispenser of FIG. 1.
Figure 47:
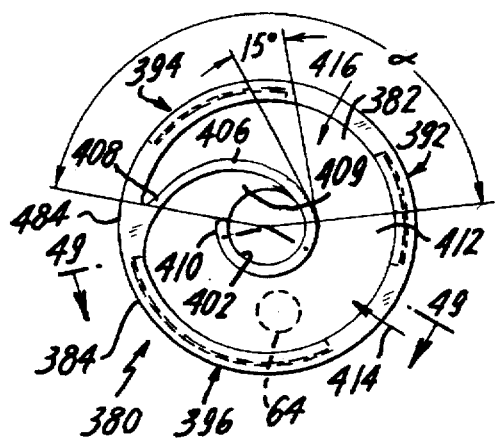
FIG. 47 is a bottom plan view of the swirl nozzle of FIG. 46.
Figure 48:
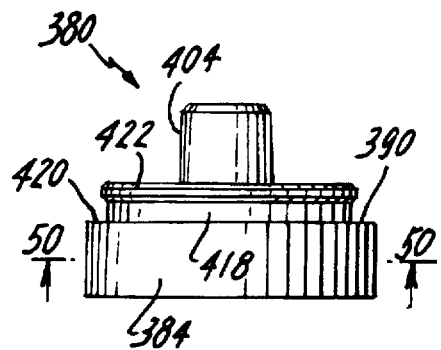
FIG. 48 is a side elevational view of the swirl nozzle of FIG. 46.
Figure 49:
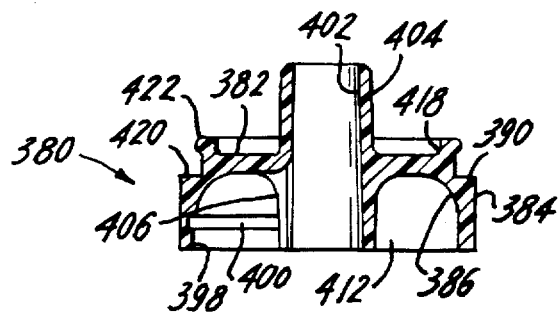
FIG. 49 is a cross-sectional view of the swirl nozzle of FIG. 47, taken along line 49—49 thereof.
Figure 50:
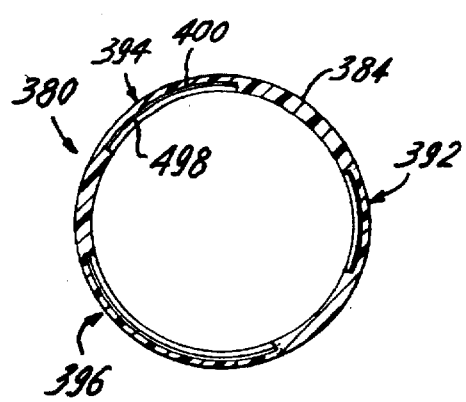
FIG. 50 is a cross-sectional view of only the annular side wall of the swirl nozzle of FIG. 48, taken along line 50—50 thereof.
Figure 51:
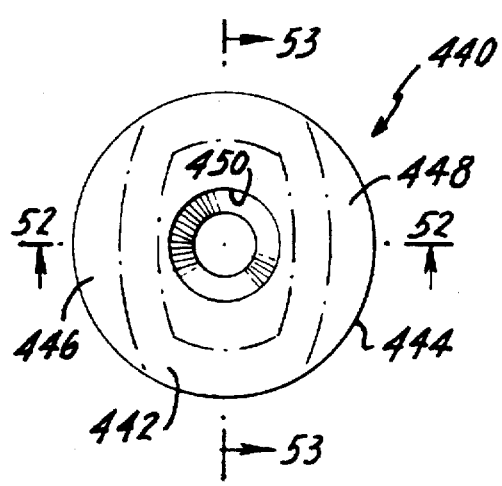
FIG. 51 is a top plan view of the mouthpiece of the metered powder dose dispenser of FIG. 1.
Figure 52:
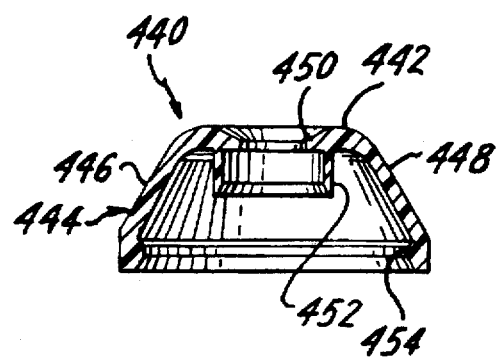
FIG. 52 is a cross-sectional view of the mouthpiece of FIG. 51, taken along line 52—52 thereof.
Figure 54:
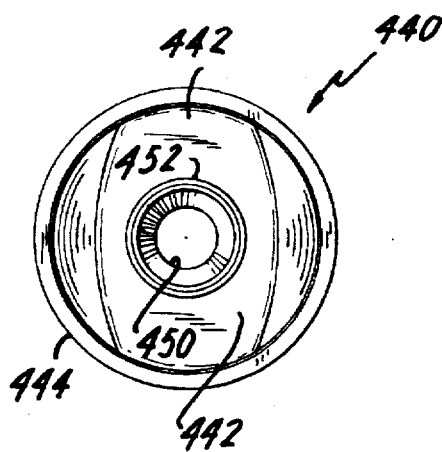
FIG. 54 is a bottom plan view of the mouthpiece of FIG. 51.
Figure 53:
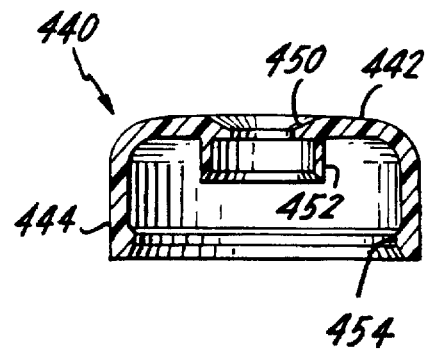
FIG. 53 is a cross-sectional view of the mouthpiece of FIG. 51, taken along line 53—53 thereof.
Figure 55:
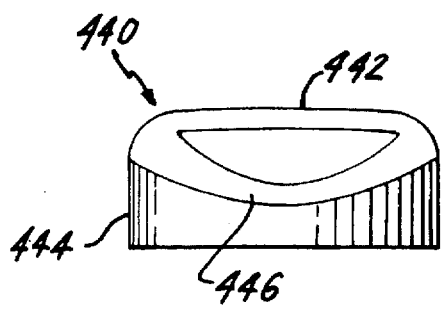
FIG. 55 is a side elevational view of the mouthpiece of FIG. 51.
Figure 56:
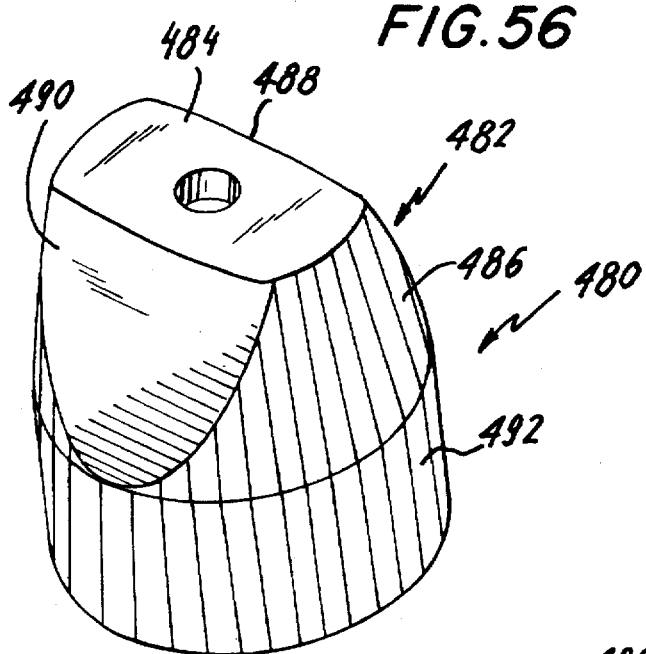
FIG. 56 is a top perspective view of a combination mouthpiece nozzle according to another embodiment of the present invention.
Figure 57:
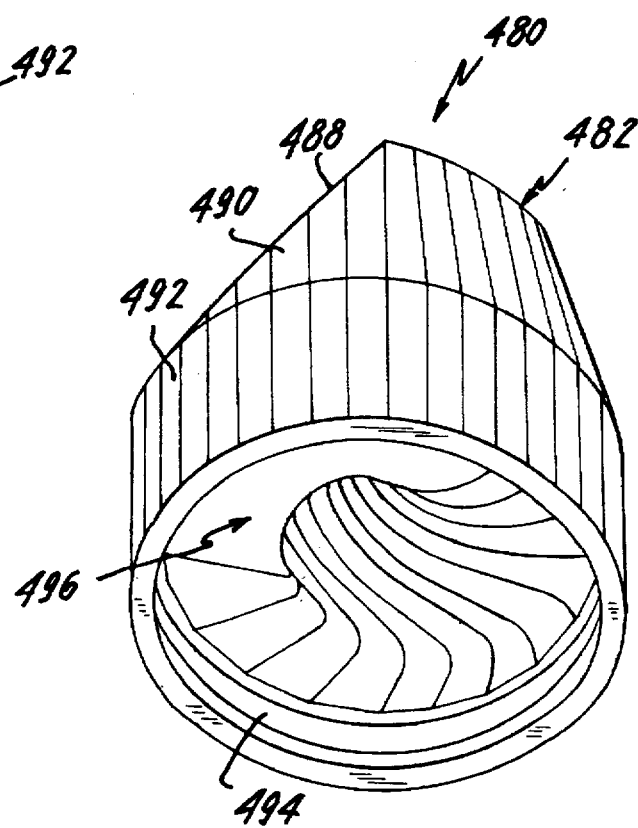
FIG. 57 is a bottom perspective view of the mouthpiece nozzle of FIG. 56.

Although the outer surfaces of plug conduits 100 and 102 are discussed above as being smooth, it will be appreciated that such outer surfaces can be formed with ribs 104, as shown in FIGS. 4, 12 and 13.

As shown in FIGS. 3, 4 and 14–21, driving body 120 includes a circular top wall 122 having an annular skirt 124 extending downwardly from the periphery of circular top wall 122.

Annular skirt 124 includes an upper annular skirt section 126 with its upper end extending downwardly from the periphery of circular top wall 122, and a lower annular skirt section 128 extending downwardly from the lower end of upper annular skirt section 126. Lower annular skirt section 128 has an inner and outer diameter greater than the inner and outer diameters, respectively, of upper annular skirt section 126. Accordingly, an inner annular shoulder 130 is formed at the lower edge of upper annular skirt section 126, along the inside of annular skirt 126. However, the outer surface of the transition area between upper annular skirt section 126 and lower annular skirt section 128 is formed as a frusto-conical surface 132.

Further, the inner diameter of lower annular skirt section 128 is substantially the same as the outer diameter of upper annular skirt section 28 of reservoir body 22 and the inner diameter of upper annular skirt section 126 is substantially the same as the outer diameter of peripheral securing wall 74 of reservoir body 22. Accordingly, reservoir body 22 fits into driving body 120 with a close fit until the radially extending annular lip 80 of peripheral securing wall 74 abuts against annular shoulder 130.

In order to lock reservoir body 22 and driving body 120 together in such position, two axially spaced apart, circumferentially extending ribs 134 and 136 are formed parallel to and spaced above annular shoulder 130, on the inner surface of upper skirt section 126, to define an annular holding area 138 therebetween. Thus, when reservoir body 22 is inserted within driving body 120 in the manner described above, lip 80 at the upper end of peripheral securing wall 74, due to the resilience of the plastic pieces, rides along the inner surface of upper skirt portion 126 and over lower rib 136, and is held between ribs 134 and 136 within annular holding area 138.

Further, to ensure proper orientation between reservoir body 22 and driving body 120, two spaced apart, axially extending, radially oriented aligning ribs 140 are provided on the inner surface of upper annular skirt section 126. Ribs 140 are spaced apart by a distance substantially equal to the width of gap 76. Thus, in the assembled condition of reservoir body 22 and driving body 120, ribs 140 fit with close tolerance between tabs 78 of reservoir body 22, that is, within gap 76.

Circular top wall 122 is formed with a circular opening 142 which is aligned with and receives frusto-conical venturi conduit 64 so that the upper edge of frusto-conical venturi conduit 64 is substantially flush with the upper surface of circular top wall 122.

A circular plug conduit 144 depends downwardly from the lower surface of circular top wall 122 and is in alignment with powder supply conduit 60. A radially extending rib 146 extends outwardly from the lower end of plug conduit 144 and has an outer diameter substantially equal to or slightly greater than the inside diameter of powder supply conduit 60. Thus, plug conduit 144 closes the upper open end of powder supply conduit 60 when reservoir body 22 is assembled with driving body 120. Therefore, powder 62 can only escape through manifold 46, opening 55 and substantially oval holes 96 and 98.

Further, a curved retaining wall 148 extends downwardly from the lower surface of circular top wall 122 in partial surrounding relation to circular opening 142 to ensure a further separation between powder supply conduit 60 and frusto-conical venturi conduit 64 when reservoir body 22 and driving body 120 are assembled.

In order to provide for secondary air flow, as will be described hereinafter, the wall defining upper annular skirt section 126 extends inwardly in the radial direction to form a first outer air passage 150 adjacent to circular opening 142 in the circumferential direction of driving body 120 and a second outer air passage 152 arcuately spaced approximately 100° from first air passage 150.

Axially extending upper securing walls 154, 156 and 158 are formed along a common circular arc at the periphery on the upper surface of circular top wall 122 in order to secure a nozzle to driving body 120, as will be described in greater detail hereinafter. Specifically, upper securing wall 154 is formed circumferentially between air passages 150 and 152; upper securing wall 156 is formed circumferentially between second outer air passage 152 and plug conduit 144; and upper securing wall 158 is formed circumferentially between first outer air passage 152 and plug conduit 144 and in outer surrounding relation to circular opening 142. A radially extending rib 160 extends outwardly from the upper end of each upper securing wall 154, 156 and 158. The common circular arc along which upper securing walls 154, 156 and 158 extend is spaced slightly from the peripheral edge of circular top wall 122 so as to define an annular retaining ledge 159 on circular top wall 122, positioned outwardly of upper securing walls 154, 156 and 158 in the radial direction.

A rotation limiting tab 162 is formed in downwardly depending relation from the lower edge of lower annular skirt section 128, the purpose for which will be apparent from the description hereinafter. Rotation limiting tab 162 includes a rounded nub 163 at the lower end thereof.

Lastly, two diametrically opposite driving recesses 164 and 166 are formed in lower annular skirt section 128, with driving recess 164 being in circumferential alignment with circular opening 142. As will be described hereinafter, driving recesses 164 and 166 are engaged to rotate driving body 120.

In order to provide metered doses of powder 62 from powder supply conduit 60 to venturi conduit 64, a metering dose plate 180 is positioned within upper annular skirt section 28 of reservoir body 22, immediately below reservoir plug 90. Specifically, metering dose plate 180 includes a thin disc 182 having a single small metered dose hole 184 near the periphery thereof which functions as a single powder receptacle, that is, for holding a metered dose of powder 62. In order to prevent the metered dose of powder from falling through dose hole 184, a powder retainer 186 is formed in covering relation to the lower surface of disc 182, extending at least over dose hole 184. Preferably, powder retainer 186 is formed by a mesh screen, filter, porous material or the like which has a minimal restrictive effect on gas flow therethrough, while preventing appreciable loss of powdered medicament below the lower surface of disc 182. Powder retainer 186 can be fabricated from any suitable material, including cellulosics, polymerics, metals, ceramics, glasses or composites thereof, exemplary useful materials including sintered porous plastics, porous polymer membranes, natural or synthetic woven fabrics, nonwoven synthetic fabrics and the like. More specifically, useful materials include polyester and polyolefin woven mesh, and porous membranes of polyolefins, polycarbonates, polytetrafluoroethylene, polyvinylidene dichloride, and mixed esters of cellulose.

An annular mounting post 188 extends downwardly from the lower surface of disc 182 and is centrally located thereon. Annular mounting post 188 is formed with a flat 190 along the length thereof, flat 190 extending an arcuate distance of approximately 65°. As will be understood from the description hereinafter, flat 190 ensures that metering dose plate 180 will remain stationary with respect to powder housing 20 when powder housing 20, which includes reservoir body 22, reservoir plug 90 and driving body 120, is rotated.

In operation, metered dose hole 184 is initially in alignment with frusto-conical venturi conduit 64. As will be explained hereinafter, powder housing 20 is only permitted to rotate 180° relative to metering dose plate 180. During initial priming rotation, metered dose hole 184 passes under manifold 46 and substantially oval holes 96 and 98. As a result, powder 62 falls within and is scraped into metered dose hole 184. Specifically, the side walls defining substantially oval holes 96 and 98 function to scrape the powder 62 into metered dose hole 184. It will be appreciated that, since oval holes 96 and 98 are spaced less than 180° from circular hole 94, metered dose hole 184 travels completely past oval holes 96 and 98 and manifold 46. Then, during the return rotation back to the initial position, metered dose hole 184 passes back under manifold 46 and substantially oval holes 96 and 98, into alignment with venturi conduit 64. During this return travel, the side walls defining substantially oval holes 96 and 98 again function to scrape the powder 62 into metered dose hole 184, thus ensuring that metered dose hole 184 is completely and accurately filled. Thus, the scraping action is provided during both counterclockwise and clockwise rotation, that is, both during the 180° loading stage and the reverse 180° movement to the inhalation stage. When metered dose hole 184 is aligned with venturi conduit 64, it is then only necessary for the user to inhale through venturi conduit 64, causing a draw and suction through metered dose hole 184, wherein the metered dose of powder 62 is drawn up through venturi conduit 64 and delivered to the user.

In order to provide for this relative rotation, metering dose plate 180 is non-rotatably mounted on, and powder housing 20 is rotatable mounted on, a base 200, shown in FIGS. 3, 4 and 25–29. Base 200 includes a circular top wall 202 having an annular skirt 204 extending downwardly from the periphery thereof. The peripheral edge of circular top wall 202 is cut-away to define an outer annular ledge 206. An annular supporting lip 208 is formed on the outer surface of annular skirt 204 at the lower end thereof, so as to extend outwardly therefrom in the radial direction of annular skirt 204. In addition, an annular retaining rim 210 is formed on the outer surface of annular skirt 204, parallel to supporting lip 208 and spaced thereabove, so as to extend outwardly from annular skirt 204 in the radial direction thereof. Retaining rim 210 has a diameter less than the diameter of supporting lip 208. Thus, an annular retaining gap 212 is formed between supporting lip 208 and retaining rim 210. Further, retaining rim 210 is cut away along a very small arcuate distance to define a small slot 214 therein, and also has a frusto-conical upper annular surface.

A cylindrical boss 216 is formed centrally and axially on the upper surface of circular top wall 202, and a coaxial retaining post 218 of lesser diameter than cylindrical boss 216 is formed at the upper end of cylindrical boss 216. Accordingly, an outer annular ledge 220 is formed at the upper edge of cylindrical boss 216. Retaining post 218 has an outer diameter slightly less than the inner diameter of annular mounting post 188 of metering dose plate 180. Retaining post 218 is formed with a flat 222 along the length thereof, flat 222 extending an arcuate distance of approximately 65°. Accordingly, due to flats 190 and 222, mounting post 188 of metering dose plate 180 is retained on retaining post 218 in a non-rotatable manner to ensure that metering dose plate 180 will remain stationary with respect to powder housing 20 when powder housing 20, which includes reservoir body 22, reservoir plug 90 and driving body 120, is rotated.

As part of a counter mechanism which will be described in greater detail hereinafter, a first rotation prevention spring detent 224 is mounted in a cantilever manner on circular top wall 202. Specifically, a curved vertical detent supporting wall 226 extends upwardly from circular top wall 202 at a position substantially midway between annular ledge 206 and cylindrical boss 216, and first rotation prevention spring detent 224 extends from one edge 228 of detent supporting wall 226, parallel to and spaced above circular top wall 202. Further, the free end of first rotation prevention spring detent 224 is provided with a bevel 230 thereat which is oriented in the radial direction of circular top wall 202.

Also as part of the counter mechanism which will be described in greater detail hereinafter, a second rotation prevention spring detent 232 is mounted in a cantilever manner on circular top wall 202. Specifically, second rotation prevention spring detent 232 extends from edge 228 of detent supporting wall 226, parallel to and spaced above circular top wall 202 and parallel to and spaced above first rotation prevention spring detent 224. The free end of second rotation prevention spring detent 232 is provided with a bevel 234 thereat which is oriented in the radial direction of circular top wall 202. It is noted particularly from FIG. 25 that the free end of detent 224 extends radially outward to a slightly greater extent than the free end of detent 232.

A sectored recess 236 is formed in circular top wall 202 in correspondence with detents 224 and 232. Specifically, recess 236 includes a first radial boundary 238 in line with the free end of detent 232, a second radial boundary 240 in line with the connected end of detent 232, and a third boundary 242 connected between the inner ends of radial boundaries 238 and 240 and extending in alignment with the lengthwise direction of detent 232.

In order to spring bias metering dose plate into engagement with the lower surface of thin circular plate 92 of reservoir plug 90 and to ensure that powder 92 can only be inhaled when metered dose hole 184 is in alignment with venturi conduit 64, a biasing assembly is provided.

The biasing assembly includes a lower spring retainer 260 mounted on annular ledge 220, over retaining post 218, as shown in FIGS. 3, 4 and 30–34. Specifically, lower spring retainer 260 includes a disc 262 having a central opening 264 sized to receive retaining post 218. An annular boss 266 extends from the lower surface of disc 262 in surrounding relation to central opening 264. When retaining post 218 extends through annular boss 266 and central opening 264, the lower edge of annular boss 266 seats upon annular ledge 220.

An upper annular retaining lip 268 extends upwardly from the peripheral edge of disc 262. Further, two radially extending driven ears 270 and 272 are formed in diametrically opposite positions at the peripheral edge of annular lip 268. Ear 270 has a width substantially equal to the width of drive slot 34 of reservoir body 22 so as to fit therein and be driven thereby, and ear 272 has a width substantially equal to the width of drive slot 36 of reservoir body 22 so as to fit therein and be driven thereby.

Further, an arcuate pawl driving wall 274 extends from the lower surface of disc 262 between annular boss 266 and the periphery of disc 262, for an arcuate distance of approximately 79°. Pawl driving wall 274 includes opposite pawl driving ends 276 and 278, as will be described in greater detail hereinafter with reference to the counter mechanism.

The biasing assembly further includes a coil spring 290 having one end seated on the upper surface of disc 262 of lower spring retainer 260, and restrained thereon by annular retaining lip 268.

As shown in FIGS. 3, 4 and 35–37, the biasing assembly further includes a support plate 300 which supports metering dose plate 180, functions as an upper spring retainer, biases metering dose plate 180 against the lower surface of thin circular plate 92 of reservoir plug 90, and permits suction through metered dose hole 184 only when metered dose hole 184 is in alignment with venturi conduit 64.

Specifically, support plate 300 is formed by a disc 302 having an annular retaining lip 304 extending downwardly from the peripheral edge of disc 302.

Two radially extending driven ears 306 and 308 are formed in diametrically opposite positions at the peripheral edge of annular lip 304. Ear 306 has a width substantially equal to the width of drive slot 34 of reservoir body 22 so as to fit therein and be driven thereby, and ear 308 has a width substantially equal to the width of drive slot 36 of reservoir body 22 so as to fit therein and be driven thereby. The height of ears 306 and 308 is less than the height of annular lip 304, and lower surfaces of ears 306 and 308 are substantially flush with the lower edge of annular lip 304, although the invention is not so limited.

In addition, a central circular hole 310 is formed in disc 302 and is sized to rotatably receive annular mounting post 188 of metering dose plate 180 therein. A radially extending slot 312 extends from and is in communication with circular hole 310. Slot 312 extends outwardly in the radial direction by a distance such that the radially outer part of slot 312 overlaps metered dose hole 184 when metered dose hole 184 is in alignment with venturi conduit 64, and is out of alignment with, and thereby does not overlap, metered dose hole 184 at all other times.

As described above, powder retainer 186 is formed by a mesh screen, filter, porous material or the like which has a minimal restrictive effect on gas flow therethrough. However, when a mesh screen or the like is used, there is a reduction in gas flow, and thereby of any suction by the user, of approximately 35%. According to an alternative embodiment, as shown in FIG. 38, powder retainer 186 comprised of a mesh screen or the like can be relocated to the lower surface of disc 302 of support plate 300, under slot 312. Therefore, although the mesh screen or the like reduces the gas flow through radially extending slot 312, this does not effectively restrict the gas flow through metered dose hole 184 which is smaller than slot 312. Thus, primary air flow is independent of the cross-sectional width of metering dose plate 180. Further, there is no mesh powder retainer 186 at metered dose hole 184 to reduce air flow through metered dose hole 184.

As shown in FIG. 39, which is an alternative embodiment of the arrangement of FIG. 38, slot 312 in support plate 300 is angled at opposite sides thereof in a downwardly diverging manner. With such arrangement, the air flow cross-sectional area at the bottom of slot 312 can be made greater than four times the air flow cross-sectional area of metered dose hole 184.

It will be appreciated from the above description that metering dose plate 180 is held stationary on base 200, due to flats 190 and 222. Further, powder housing 20, comprised of reservoir body 22, reservoir plug 100 and driving body 120, is rotatably mounted with respect to base 200 and metering dose plate 180.

In addition, support plate 300 is biased into engagement with the lower surface of metering dose plate 180 so as to support the same. In the operation, radially extending slot 312 is in alignment with metered dose hole 184 only when metered dose hole 184 is in alignment with venturi conduit 64. Thus, any powder 62 within metered dose hole 184 when metered dose hole 184 is out of alignment with venturi conduit 64 is sandwiched in metered dose hole 184 by mesh powder retainer 186 and the upper surface of disc 302 of support plate 300 at its lower end, and by the lower surface of thin circular plate 92 of reservoir plug 90 at its upper end. As will be discussed in greater detail hereinafter, in the stored or inactive position of metered powder dose dispenser 10, metered dose hole 184 is primed, and is positioned diametrically opposite to radially extending slot 312. In such position, powder 62 within metered dose hole 184 is held between the upper surface of disc 302 of support plate 300 and the lower surface of thin circular plate 92 of reservoir plug 90, and therefore cannot escape metered dose hole 184.

In order to positively hold all of the above elements together, metered powder dose dispenser 10 further includes an adapter 320, as shown in FIGS. 3, 4 and 40–45. As shown therein, adapter 320 includes a lower annular wall 322 having an inner diameter larger than the outer diameter of lower annular skirt section 30 of reservoir body 22 so as to easily fit thereover. The inner diameter of lower annular wall 322 is also slightly larger than the outer diameter of annular skirt 204 of base 200 so as to fit thereover, but slightly less than the outer diameter of annular retaining rim 210 of base 200. Further, the inner, lower edge of lower annular wall 322 is beveled at 323.

An annular groove 324 is formed at the lower end of lower annular wall 322, slightly spaced above the lower edge thereof. Accordingly, due to the resilience of the plastic pieces, when adapter 320 is inserted over base 200 and pushed down thereon, retaining rim 210 of base 200 snaps into annular groove 324 to hold adapter 320 on base 200. In order to obtain and maintain correct alignment between adapter 320 and base 200, adapter 320 is provided with a small bridge 326 within groove 324. Bridge 326 has a width substantially equal to that of small slot 214 in base 200 so as to fit therein. Thus, rotation of adapter 320 causes base 200 to rotate therewith.

The outer surface of lower annular wall 322 is preferably provided with a gripping surface 328 formed by undulations, knurling or the like, to enhance the gripping and rotation of metered powder dose dispenser 10.

An oval transparent plastic window 330 is provided in lower annular wall 322, substantially diametrically opposite to bridge 326, and substantially centrally along the height of lower annular wall 322 for use with the counter mechanism which will be described in greater detail hereinafter.

Adapter 320 further includes an upper annular wall 332 of a lesser diameter than lower annular wall 322, and connected to the upper end of lower annular wall 322 by an annular frusto-conical connecting section 334. As will be apparent from the description hereinafter with respect to the counter mechanism, a dosage limiter tab 336 is formed above window 330 on the inner surfaces of connecting section 334 and lower annular wall 322. Dosage limiter tab 336 prevents operation of metered powder dose dispenser 10 after a prescribed number of doses, for example 200 doses, have been dispensed; this is sometimes referred to herein as a "lock-out" feature.

An annular biasing lip 338 is formed on the inner surface of upper annular wall 332. When adapter 320 is pushed down so as to lock adapter 320 onto base 200, as described above, annular biasing lip 338 seats on outer annular shoulder 32 of reservoir body 22, and thereby biases reservoir body 22 down against the force of coil spring 290. Accordingly, coil spring 290 is compressed so that a biasing force always forces support plate 300 into abutment with metering dose plate 180, and always forces metering dose plate 180 into abutment with reservoir plug 90. However, such biasing action still permits rotation of reservoir body 22 relative to adapter 320 and metering dose plate 180.

At the same time, this compression ensures that driven ears 270 and 306 will always be located within drive slot 34 and driven ears 272 and 308 will always be located within drive slot 36, so that rotation of reservoir body 22 will cause consequent rotation of lower spring retainer 260 and support plate 300. Because metering dose plate 180 is held stationary on base 200, due to flats 190 and 222, powder housing 20 (comprised of reservoir body 22, reservoir plug 100 and driving body 120), lower spring retainer 260 and support plate 300, are rotatably mounted with respect to base 200, metering dose plate 180 and adapter 320.

In the assembled condition discussed above, the lower edge of lower annular skirt section 128 of driving body 120 rests and rotates on the upper edge of upper annular wall 332 of adapter 320. In order to provide air flow through metered dose hole 184 of metering dose plate 180, two diametrically opposite recesses 340 and 342 are formed in upper annular wall 332, extending from the upper edge of upper annular wall to annular biasing lip 338. Recess 340 has a width identical to the width of drive slot 34, while recess 342 has a width identical to the width of drive slot 36. When metered dose hole 184 is aligned with venturi conduit 64 of reservoir body 22 and with radially extending slot 312 of support plate 300, recess 340 is in alignment with drive slot 34 and recess 342 is in alignment with drive slot 36. Accordingly, suction on venturi conduit 64 causes air to flow through recess 340 and drive slot 36 and through recess 342 and drive slot 36, and then through radially extending slot 312, metered dose hole 184 and venturi conduit 64 to deliver the metered dose of powder 62 in metered dose hole 184, to a user of dispenser 10.

When the lower edge of lower annular skirt section 128 of driving body 120 rests and rotates on the upper edge of upper annular wall 332 of adapter 320, rotation limiting tab 162, and rounded nub 163 thereof, ride along the upper surface of annular biasing lip 338. In this regard, two stops 344 and 346 are formed on the upper surface of annular biasing lip 338 such that opposite ends of rotation limiting tab 162 abut thereagainst during rotation of driving body 120 relative to adapter 320, in order to limit rotation of powder housing 20 to a clockwise and counterclockwise rotation of 180°.

In order to prevent accidental rotation of driving body 120 relative to adapter 320, two detents 348 and 350 of a small height are provided on the upper surface of annular biasing lip 338, slightly spaced from stops 344 and 346, respectively. Accordingly, during rotation of driving body 120 relative to adapter 320, rounded nub 163 at the lower end of rotation limiting tab 162 is caused to ride over detents 348 and 350 due to resilience of the plastic parts. Rotation limiting tab 162 is thereby releasably held between stop 344 and detent 348, or releasably held between stop 346 and detent 350.

Lastly, a double helical thread 352 is formed on the outer surface of upper annular wall 332, the purpose for which will become apparent from the description which follows.

In order to ensure that the powder is de-agglomerated and properly mixed with the suction air from the open upper end of upper venturi conduit section 68 of venturi conduit 64, a swirl nozzle 380 is mounted to the upper end of reservoir body 22. Air which contains agglomerated powder particles flows from upper venturi conduit section 68 into the swirl nozzle. Mechanical de-agglomeration is an important function of the swirl nozzle.

Swirl nozzle 380 includes a circular top wall 382 and an annular side wall 384 extending downwardly from the periphery of top wall 382. Annular side wall 384 has an outer diameter substantially equal to the outer diameter of upper annular skirt section 126 of driving body 120. Further, the inner connecting region 386 between circular top wall 382 and annular side wall 384 is curved to provide a smooth transition therebetween and thereby to provide a smooth flow path for powder 62. In other words, the inner area defined by circular top wall 382, annular side wall 384 and inner connecting region 386 has a somewhat partial toroidal configuration. The outer connecting region 390 therebetween, however, forms a substantially right angle in cross-section between circular top wall 382 and annular side wall 384.

In order to secure swirl nozzle 380 onto the upper end of driving body 120, and particularly, onto annular retaining ledge 159 of driving body 120, three recessed sections 392, 394 and 396 are formed on the inner surface of annular side wall 384. Recessed sections 392, 394 and 396 extend arcuate distances which are different from each other and which correspond identically with the arcuate distances of upper securing walls 154, 156 and 158 of driving body 120. Further, recessed sections 392, 394 and 396 are spaced apart in an identical manner to upper securing walls 154, 156 and 158 of driving body 120.

Each recessed section 392, 394 and 396 includes a lower arcuate cut-away area 398 that extends upwardly along the inner surface of annular side wall 384 from the lower edge thereof. Thus, each cut-away area 398 has a wall thickness less than the wall thickness of annular side wall 384 at positions outside of recessed sections 392, 394 and 396. Each recessed section 392, 394 and 396 further includes an upper arcuate groove 400 formed by cutting away an area of each recessed section 392, 394 and 396 immediately above cut-away area 398. In other words, each arcuate groove 400 is formed so that the wall thickness of annular side wall 384 thereat is less than the wall thickness of cut-away area 398.

It will therefore be appreciated that swirl nozzle 380 is snap fit onto driving body 120. Specifically, recessed sections 392, 394 and 396 are aligned with upper securing walls 154, 156 and 158 of driving body 120. When a downward axial force is applied to swirl nozzle 380, and due to the resilience of the plastic elements, radially extending ribs 160 of upper securing walls 154, 156 and 158 ride over cut-away areas 398 and into arcuate grooves 400, so as to retain swirl nozzle 380 on driving body 120. It will be appreciated that, in such position, first and second outer air passages 150 and 152 extend inwardly of annular side wall 384 to supply secondary air flow thereto which mixes with the air/powder mixture from venturi conduit 64 which is also supplied to the interior of annular side wall 384.

Circular top wall 384 has a central opening 402, and a supply chimney 404 is formed on the upper surface of circular top wall 384 in surrounding relation to central opening 402.

In order to break up the powder agglomerates, prior to supplying the same through supply chimney 404, a curved spiral-like wall 406 extends downwardly from circular top wall 382 and is connected at one end 408 to annular side wall 384. Specifically, curved wall 406 extends in a curvilinear manner from end 408, and partially about central opening 402 to an opposite end 410. Thus, a gap 409 is provided between end 410 and the remainder of curved wall 406. The height of curved wall 406 is equal to that of annular side wall 384 so that the lower edge of curved wall 406 sits on circular top wall 122 of driving body 120 when swirl nozzle 380 is assembled with driving body 120, as described above. Curve wall 406 is effectively formed in two sections, namely, a first section 406a extending partially about central opening 402, for example, for 165°, and a second section 406b extending from one end of first section 406a to the inner surface of annular side wall 384 along a larger radius than first section 406a. With respect to the direction of the radius to the center of venturi conduit 64, second section 406b preferably leaves or disengages from central opening 402 at an angle of approximately 15° parallel to such radius line, regardless of the size of swirl nozzle 380.

Figure 58:
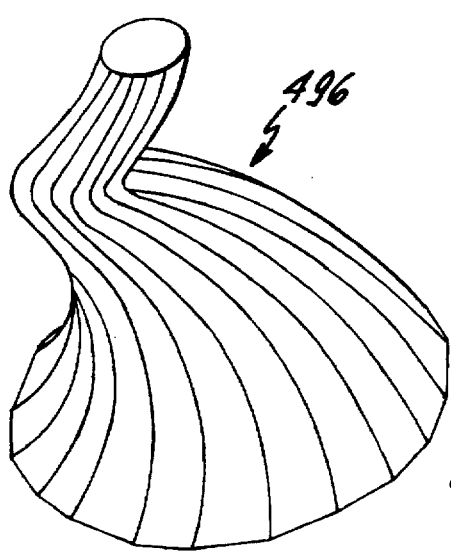
FIG. 58 is a perspective view of the shape of the internal swirl cavity of the mouthpiece nozzle of FIG. 56.
Figure 59:
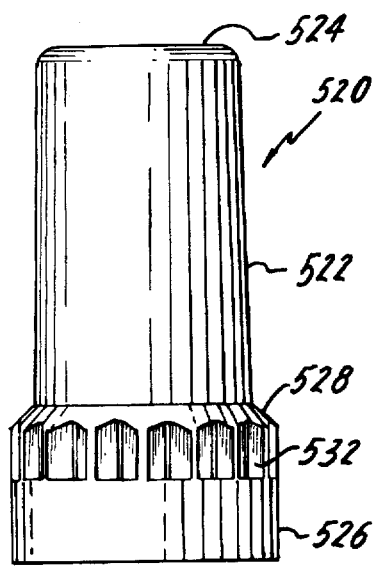
FIG. 59 is a side elevational view of the closure cap of the metered powder dose dispenser of FIG. 1.
Figure 60:
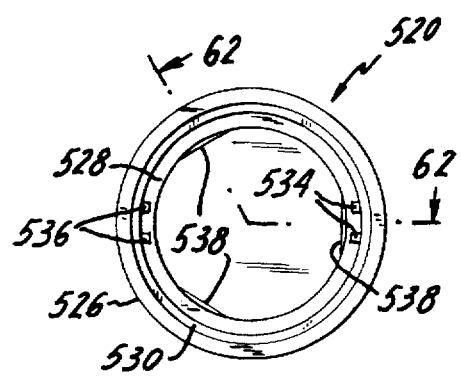
FIG. 60 is a bottom plan view of the closure cap of FIG. 59.
Figure 61:
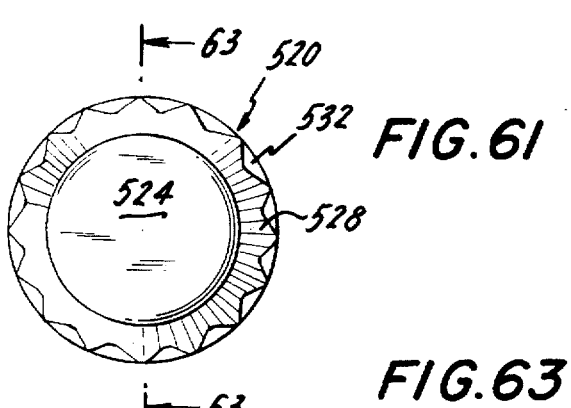
FIG. 61 is a top plan view of the closure cap of FIG. 59.
Figure 62:
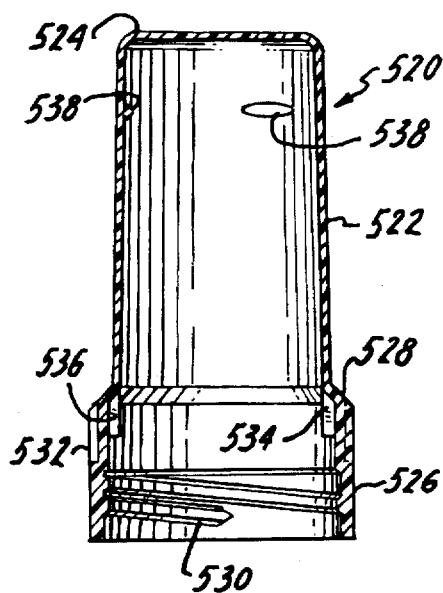
FIG. 62 is a cross-sectional view of the closure cap of FIG. 60, taken along line 62—62 thereof.
Figure 63:
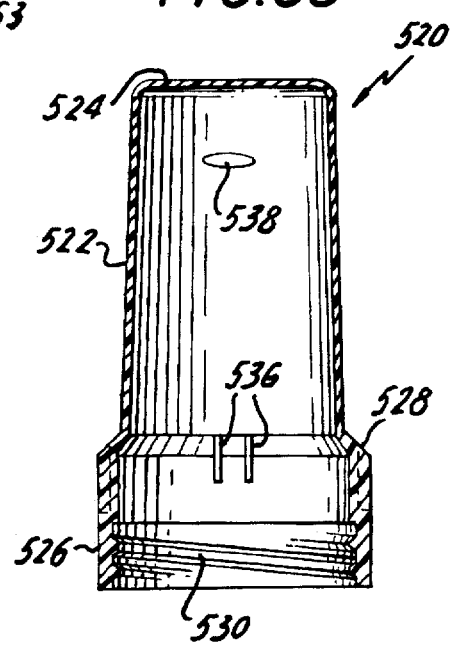
FIG. 63 is a cross-sectional view of the closure cap of FIG. 61, taken along line 63—63 thereof.
Figure 67:
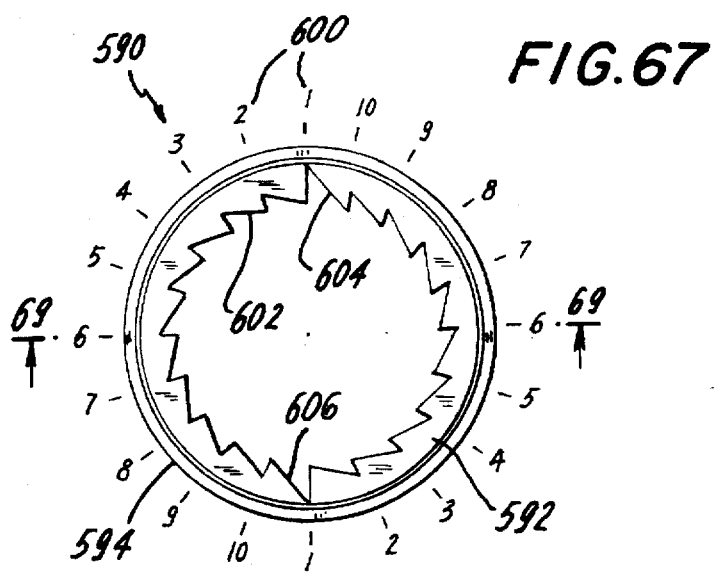
FIG. 67 is a top plan view of the continuous counter ring of the metered powder dose dispenser of FIG. 1.
Figure 69:
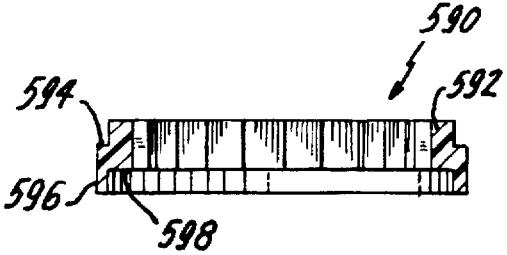
FIG. 69 is a cross-sectional view of the continuous counter ring of FIG. 67, taken along line 69—69 thereof.
Figure 68:
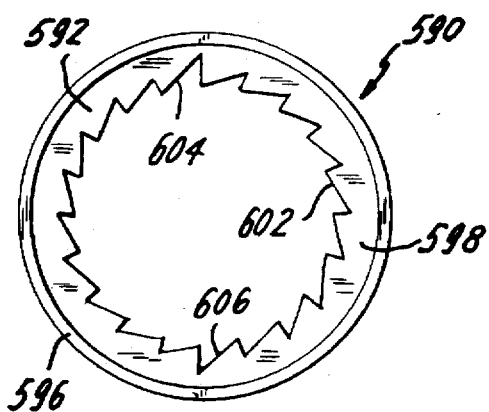
FIG. 68 is a bottom plan view of the continuous counter ring of FIG. 67.
Figure 70:
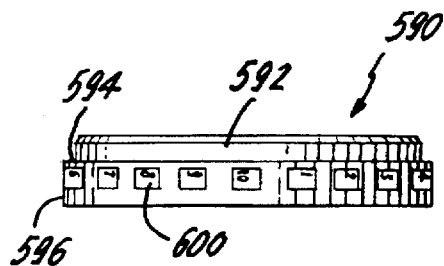
FIG. 70 is a side elevational view of the continuous counter ring of FIG. 67.
Figure 71:
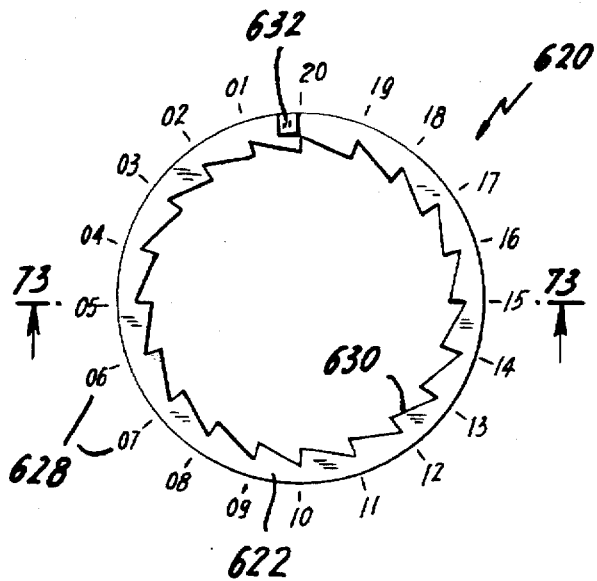
FIG. 71 is a top plan view of the intermittent counter ring of the metered powder dose dispenser of FIG. 1.
Figure 73:
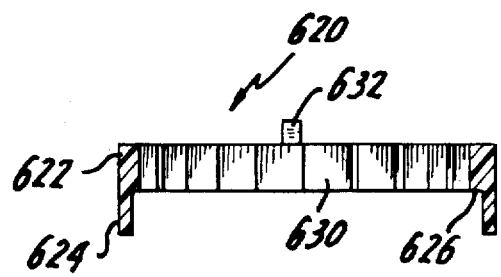
FIG. 73 is a cross-sectional view of the intermittent counter ring of FIG. 71, taken along line 73—73 thereof.
Figure 72:
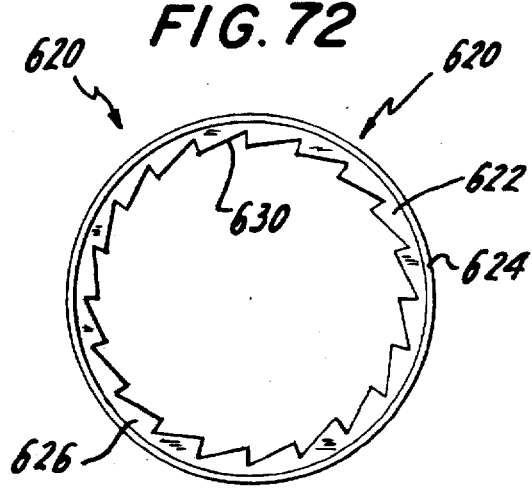
FIG. 72 is a bottom plan view of the intermittent counter ring of FIG. 71.

As will be appreciated, curved wall 406 defines a swirl cavity 412, such that the powder from venturi conduit 64 enters swirl cavity 412 and continuously changes direction as it increases in velocity, prior to entering supply chimney 404. Thus, the powder agglomerates constantly impact against circular top wall 382, annular side wall 384 and curved wall 406 within swirl cavity 412. Further, the agglomerates collide with each other which results in a mutual grinding or shattering action between the agglomerates. At the same time, secondary air flow from first and second outer air passages 150 and 152 enters swirl chamber 412, as indicated by arrows 414 and 416, respectively, to accelerate movement of the powder agglomerates in swirl cavity 412. The constant impacts of the powder agglomerates on the walls defining swirl cavity 412 cause the agglomerates to break up into micronized powder upon impact. Basically, as long as the powder agglomerates travel with sufficient velocity, there will be sufficient kinetic energy to break up the agglomerates.

Further, rather than providing a merely helical path along the axial direction of a nozzle, as in the prior art, curved wall 406 and, particularly, swirl cavity 412, first changes the direction of powder 62 from an axial direction of venturi conduit 64 to a transverse direction substantially perpendicular to the axial direction. In this transverse direction, powder 62 is then forced to continuously change direction in the transverse direction of swirl cavity 412. Upon exiting swirl cavity 412, the direction of powder 62 is again changed to an axial direction through supply chimney 404, while retaining a swirl component of the flow, that is, while swirling spirally through chimney 404. Since the micronized powder and any remaining agglomerates maintain the swirl imparted thereto from swirl cavity 412, the swirling flow applies a centrifugal force to the micronized powder and remaining agglomerates, creating additional impacts in supply chimney 404 so as to result in further breaking up of the remaining agglomerates.

Most of the agglomerate break-up should take place, however, in swirl cavity 412. The velocity attained by an agglomerate depends on the drag or suction force, the inertia of the agglomerate, and the length of swirl cavity 412, that is, the time the drag force acts on the agglomerate. Because of its inertia, the agglomerate impacts a wall in swirl cavity 412 to convert the same to micronized powder.

In addition to breaking up agglomerates, swirl nozzle 380 must meet additional constraints. For example, the pressure drop through the powder inhaler should desirably be lower than about 20 inches of a water column (5 Kpa) for ease of use by persons with impaired respiratory function, yet sufficiently high to permit significant primary air flow through metered dose hole 184. The pressure drop through swirl nozzle 380 can be changed by varying the angle αbetween end 410 of first section 406a of curved wall 406 and the position where first section 406a and second section 406b of curved wall 406 meet, that is, where second section 406b leaves central opening 402, as shown in FIG. 47. In a presently preferred embodiment, α is about 165°, although this value may change depending upon the required pressure drop.

Further, an annular mouthpiece securing wall 418 is formed on the upper surface of circular top wall 382, spaced slightly inwardly from the peripheral edge thereof. As a result, an annular ledge 420 is formed on the upper surface of circular top wall 382, outwardly of annular mouthpiece securing wall 418. Further, an annular lip 422 extends outwardly in the radial direction from the upper end of annular mouthpiece securing wall 418.

A mouthpiece 440, as shown in FIGS. 3, 4 and 51–55, is secured to the upper end of swirl nozzle 380. Mouthpiece 440 includes a generally rectangular top wall 442 with an annular side wall 444 depending downwardly from the periphery of top wall 442. Because top wall 442 has a generally rectangular configuration and because of the annular configuration of side wall 444, upper portions at opposite sides 446 and 448 of side wall 444 corresponding to the lengthwise sides of top wall 442 slope upwardly in a diverging manner toward each other. The lips of a user of the device are placed on sides 446 and 448 during inhalation. Of course, since the user's mouth is placed over mouthpiece, the various edges thereof are rounded.

An opening 450 is centrally formed in top wall 442, the upper part of which has a frusto-conical shape and the lower part of which has a circular shape, as shown in FIGS. 52 and 53. An annular connecting tube 452 is formed at the lower surface of top wall 442 in surrounding relation to opening 450. When mouthpiece 440 is seated on swirl nozzle 380, connecting tube 452 receives the upper end of supply chimney 404 of swirl nozzle 380 therein.

In order to secure mouthpiece 440 to swirl nozzle 380, the lower end of side wall 444 has a circular or annular shape. At the inner surface of this lower end of side wall 444, there is formed an annular V-shaped projection 454 which extends inwardly in the radial direction. When mouthpiece 440 is positioned on swirl nozzle 380 and pressed down thereon, annular lip 422 of swirl nozzle 380, due to resilience of the plastic pieces, rides over V-shaped projection 454, so that V-shaped projection 454 retains annular lip 422, and thereby mouthpiece 440, on swirl nozzle 380. In such position, the lower edge of side wall 444 sits on annular ledge 420 of swirl nozzle 380.

An alternative embodiment of nozzle 380 and mouthpiece 440 is shown in the combination mouthpiece nozzle 480 shown in FIGS. 56–58. Specifically, mouthpiece nozzle 480 includes an upper section 482 having a similar outer shape and dimensions to those of mouthpiece 440. In this regard, upper section 482 of mouthpiece 480 includes a generally rectangular top wall 484 with a cylindrical side wall 486 depending downwardly from the periphery of top wall 484. Because top wall 484 has a generally rectangular configuration and because of the annular configuration of side wall 486, opposite sides 488 and 490 of side wall 486 corresponding to the lengthwise sides of top wall 484 slope upwardly in a diverging manner toward each other. The lips of a user of the device are placed on sides 488 and 490 during inhalation. Of course, since the user's mouth is placed over mouthpiece, the various edges thereof are preferably rounded.

Mouthpiece nozzle 480 further includes a lower section 492 formed at the lower end of upper section 482. Lower section 492 includes a retaining groove 494 along the inner surface thereof, which serves the same purpose as upper arcuate groove 400 of swirl nozzle 380. In other words, due to the resilience of the plastic elements, radially extending ribs 160 of upper securing walls 154, 156 and 158 of driving body 120 are inserted within retaining groove 494, so as to retain mouthpiece nozzle 480 on driving body 120.

A swirl cavity 496 is formed inside of mouthpiece nozzle 480 at a position above retaining groove 494. The interior surface contour of swirl cavity 496 resembles the shape of an inverted tornado, as shown in FIG. 58. Specifically, the interior surface contour is a continuously changing circle, the radius of which changes exponentially by depth from a lower outer circle of radius $c_0+c_1$ to an upper circle of radius $c_0$. The origin of the continuously changing circle is denoted by designators a and b which correspond to the x and y coordinates. This origin (a,b) itself moves in a circle which changes with depth. Therefore, not only does the radius change with depth, but also, the origin of the circle also changes with depth.

The equation for the interior surface contour is as follows:

$$(x-a)^2+(y-b)^2=c_0+c_1*e^{-kz},$$

where $a=a_0*\text{sine }(a_1*\pi)$ and $b=b_0*\text{cosine }(b_1*\pi)$.

The exponential coefficient k defines the geometry of the tornado spiral, and for an upper radius of approximately 6.35 mm (¼ inch) and a lower radius of approximately 25.4 mm (one inch), a value of k equal to 13 was found to operate satisfactorily.

It will be appreciated that the above equation is a variation on the general equation for a circle, that is $x^2+y_2=r$, where r is the radius of the circle. The additional terms at the left of the tornado equation take into account the changing center of the circle, while the additional terms at the right take into account the changing height or depth of the circle. Thus, for the initial height of z=0 at the lower, larger radius end of the interior surface contour, $e^{-kz}$ equals 1, so that the right side of the equation reduces to $c_0+c_1$, which is the radius at the bottom of the interior surface contour. On the other hand, at the top, it is assumed that z=∞, whereby $c_1*e^{-kz}=0$, so that the radius at the upper end of the interior surface contour is equal to $c_0$.

With this arrangement, the outlet of venturi conduit 64 directly discharges into the tornado swirl cavity 496. During travel therethrough, the agglomerates impact against the walls defining the interior surface contour of swirl cavity 496, thereby breaking up the agglomerates into micronized powder.

It will be appreciated by those having skill in the art that the mouthpieces can readily be altered to permit nasal delivery of the medicaments, without changing the internal configuration and dimensions of the swirl nozzles. Only the exterior size and shape of the mouthpiece will require modification for nasal delivery.

Referring now to FIGS. 59–63, a closure cap 520 of metered powder dose dispenser 10 is provided as a closure for mouthpiece 440, and at the same time, functions to prime metered powder dose dispenser 10 for use. Specifically, closure cap 520 includes an upper elongated annular covering wall 522 which is closed at its upper end by a generally circular top wall 524. A lower annular securing skirt 526 of a larger diameter than annular covering wall 522, is secured to the lower end of annular covering wall 522 through an annular frusto-conical connector 528. The lower end of annular securing skirt 526 is open. Further, the inner diameter of lower annular securing skirt 526 is slightly larger than the outer diameter of upper annular wall 332 of adapter 320 so as to fit thereover.

In order to secure closure cap 520 onto metered powder dose dispenser 10, and particularly, in covering relation to mouthpiece 440, a double helical thread 530 is formed on the inner surface of lower annular securing skirt 526. Thus, when closure cap 520 is inserted over powder housing 20, swirl nozzle 380 and mouthpiece 440, helical thread 530 of closure cap 520 threadedly engages with double helical thread 352 of adapter 320, until the lower edge of lower annular securing skirt 526 seats on the annular frusto-conical connecting section 334 of adapter 320. It will be appreciated that the outer diameter of lower annular securing skirt 526 is substantially identical with the outer diameter of lower annular wall 322 of adapter 320 to provide a relative smooth, continuous appearance. In order to aid in the removal and closing of closure cap 520, the outer surface of lower annular securing skirt 526 is formed with a gripping surface 532 formed by undulations, knurling or the like, to enhance the gripping and rotating of closure cap 520.

As discussed above, closure cap 520 also serves to prime metered powder dose dispenser 10 for use. Specifically, a first pair of parallel, axially extending, spaced apart priming ribs 534 are formed on the inner surface of closure cap 520, extending a small distance down from frusto-conical connector 528 onto lower annular securing skirt 526. A second pair of parallel, axially extending, spaced apart priming ribs 536 are also formed on the inner surface of closure cap 520, extending a small distance down from frusto-conical connector 528 onto lower annular securing skirt 526, in diametrically opposite relation to priming ribs 534. The priming ribs 534 and 536 of each pair are spaced apart by a distance substantially equal to the width of driving recesses 164 and 166, respectively, of driving body 120, and fit thereinto when closure cap 520 is positioned and slightly threaded onto adapter 320. In other words, during the initial threading operation, priming ribs 534 and 536 fall into recesses 164 and 166.

When closure cap 520 is removed from metered powder dose dispenser 10, metered dose hole 184 is in alignment with venturi conduit 64, ready for inhalation by the user. When closure cap 520 is threaded back onto adapter 320, priming ribs 534 and 536 fall into driving recesses 164 and 166 of driving body 120. Thus, closing rotation of closure cap 520 causes the same rotation of driving body 120, and thereby of venturi conduit 64 relative to metered dose hole 184, to the stored position, 180° out of alignment. As discussed above, during this travel, powder 62 is scraped into metered dose hole 184, so that metered powder dose dispenser 10 is primed.

When the user is ready to use metered powder dose dispenser 10, closure cap 520 is unscrewed from adapter 320. During such movement, priming ribs 534 and 536, which are engaged with driving recesses 164 and 166 of driving body 120, cause opposite rotation of driving body 120, and thereby of venturi conduit 64 relative to metered dose hole 184, to a position in alignment. Thus, as soon as closure cap 520 is removed, metered dose hole 184, which is filled with powder 62, is in alignment with venturi conduit 64, and ready for inhalation. There is thus no need to provide any additional priming and set-up operation after closure cap 520 is removed. Of course, dispenser 10 could be operated with cap 520 removed by rotating powder housing 20 back and forth relative to adapter 320.

Further, closure cap 520 includes three equiangularly spaced protrusions 538 formed at the inner surface of covering wall 522, spaced a small distance from top wall 524.

To protect powder 62 against moisture contamination, a desiccant holder 560 is held by protrusions 538 within closure cap 520. As shown in FIGS. 64–66, desiccant holder 560 includes a circular top wall 562 and an annular side wall 564 extending down from the periphery thereof. An annular recess 566 is formed in the inner surface of annular side wall 564 at the lower end thereof for receiving a disc (not shown) which holds a desiccant, such as silica gel, therein. An annular rib 568 is formed on the outer surface of annular side wall 564. In this manner, desiccant holder 560 is inserted within closure cap 520. Due to the resilience of the plastic pieces, annular rib 568 rides over protrusions 538, so that desiccant holder 560 is held within closure cap 520 adjacent top wall 524 thereof.

A slight modification to desiccant holder 560 is shown in the assembled view of FIG. 4, in which an annular groove 570 is formed on the inner surface of annular side wall 564 to hold a disc 572 containing the desiccant.

In accordance with the present invention, a counter mechanism 580 is provided for counting the number of doses that have been dispensed or indicating the number of doses that remain to be dispensed, so as to warn the user of impending powder depletion. Many types of mechanical and electrical counters are useful. A digital electronic counter can be disposed within the base or other areas of the device, and will require electrically conductive contacts which complete a circuit at some point in the dose loading operation; the characteristics of the required battery will be a factor in establishing a shelf life for the device. Presently preferred is counter mechanism 580, a decrementing mechanical counter that indicates the number of doses remaining to be dispensed.

Counter mechanism 580 is comprised of the aforementioned first and second rotation prevention spring detents 224 and 232 on base 200, the aforementioned transparent plastic window 330 of adapter 320, a continuous counter ring 590, an intermittent counter ring 620 and a spring-biased pawl assembly 640.

As shown in FIGS. 3, 4 and 67–70, continuous counter ring 590 is formed by a disc 592 having a wall with a substantially rectangular cross-section. An outer annular ledge 594 is formed on the outer, upper edge of disc 592 by cutting away disc 592 thereat. Further, a lower annular lip 596 axially extends from the lower, outer edge of disc 592, as a smooth extension of disc 592, but of a lesser cross-sectional width. As a result, an inner annular ledge 598 is formed at the lower edge of disc 592. In this regard, continuous counter ring 590 can be seated on base 200, and in particular, inner annular ledge 598 seats upon circular top wall 202 of base 200 and lower annular lip 596 seats on annular ledge 206 of base 200 in surrounding relation to circular top wall 202.

A plurality of numerical indicia 600 are printed on the smooth combined outer surface of disc 592 and lower annular lip 596. Specifically, two successive sets of numbers "0" through "9" are printed equiangularly thereabout. It will be appreciated, however, that counting indicia other than numerical indicia 600, can be used, such as color designations, shape designations, Roman numerals, days of the week, and the like.

Twenty gear teeth 602 are equiangularly formed on the inner surface of disc 592 in correspondence with the twenty numbers of numerical indicia 600. All gear teeth 602 have the same depth in the radial direction, with the exception that diametrically opposite gear teeth 604 and 606 of gear teeth 602, corresponding to the opposite numbers "1" of numerical indicia 600, are deeper than the remaining gear teeth 602, that is, gear teeth 604 and 606 extend outwardly in the radial direction to a greater extent than the remaining gear teeth 602. When continuous counter ring 590 is seated on base 200, first rotation prevention spring detent 224 of base 200 engages with one gear tooth 602 at a time, to prevent clockwise rotation of continuous counter ring 590 on base 200.

As shown in FIGS. 3, 4 and 71–74, intermittent counter ring 620 is formed by a disc 622 having a wall with a substantially rectangular cross-section. A lower annular lip 624 axially extends from the lower, outer edge of disc 622, as a smooth extension of disc 622, but of a lesser cross-sectional width. As a result, an inner annular ledge 626 is formed at the lower edge of disc 622. In this regard, intermittent counter ring 620 can be rotatably seated on continuous counter ring 590, and in particular, inner annular ledge 626 is spaced above continuous counter ring 590, while lower annular lip 624 seats on outer annular ledge 594 of continuous counter ring 590.

Figure 74:
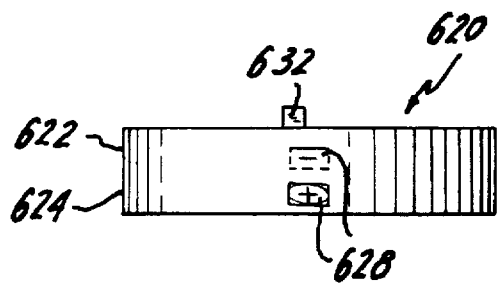
FIG. 74 is a side elevational view of the intermittent counter ring of FIG. 71.
Figure 75:
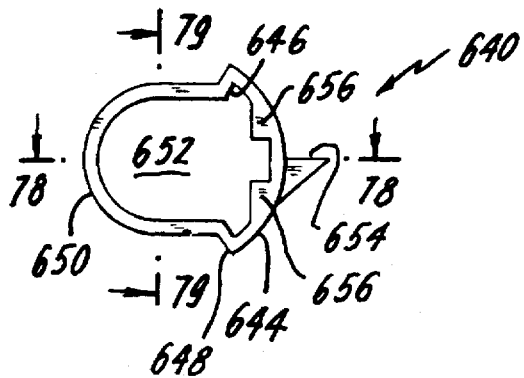
FIG. 75 is a top plan view of the pawl assembly of the metered powder dose dispenser of FIG. 1.
Figure 76:
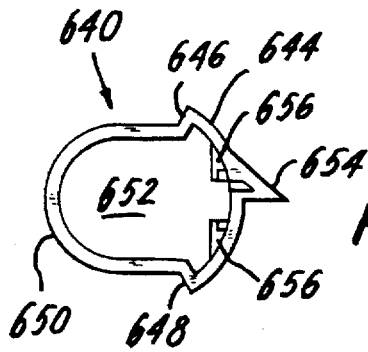
FIG. 76 is a bottom plan view of the pawl assembly of FIG. 75.
Figure 77:
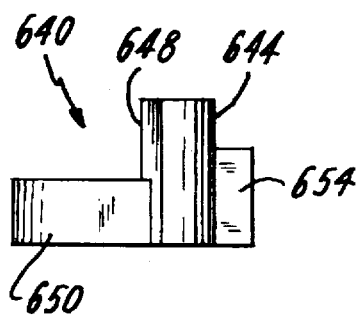
FIG. 77 Is a side elevational view of the pawl assembly of FIG. 75.
Figure 78:
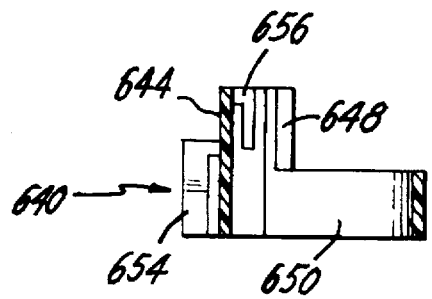
FIG. 78 is a cross-sectional view of the pawl assembly of FIG. 75, taken along line 78—78 thereof.
Figure 79:
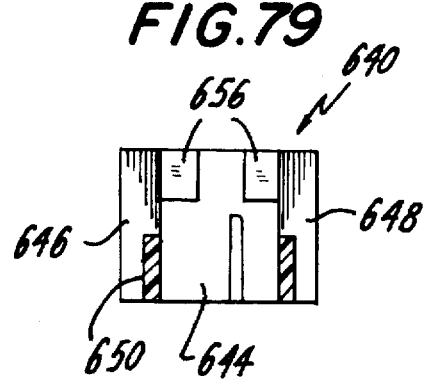
FIG. 79 is a cross-sectional view of the pawl assembly of FIG. 75, taken along line 79—79 thereof.
Figure 88:
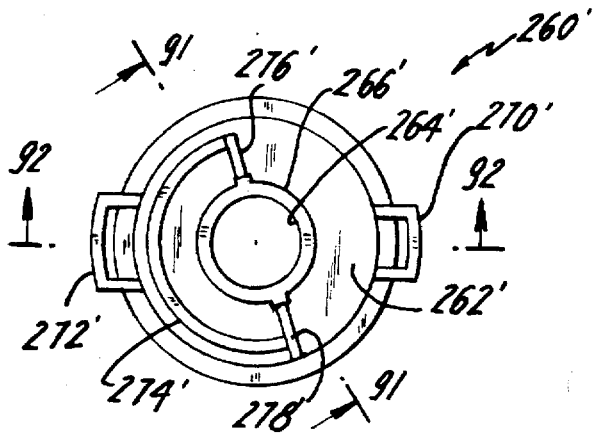
FIG. 88 is a bottom plan view of the lower spring retainer according to another embodiment of the metered powder dose dispenser of FIG. 1.
Figure 89:
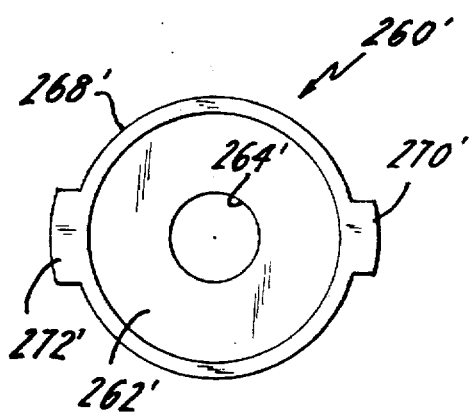
FIG. 89 is a top plan view of the lower spring retainer of FIG. 88.
Figure 90:
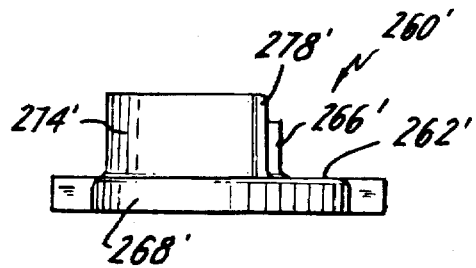
FIG. 90 is a side elevational view of the lower spring retainer of FIG. 88.
Figure 91:
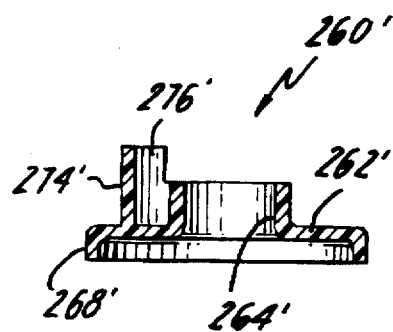
FIG. 91 is a cross-sectional view of the lower spring retainer of FIG. 88, taken along line 91—91 thereof.
Figure 92:
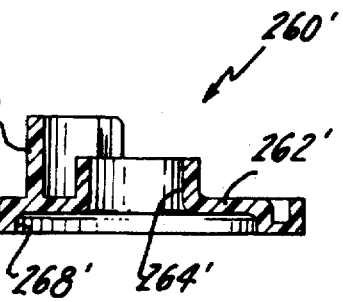
FIG. 92 is a cross-sectional view of the lower spring retainer of FIG. 88, taken along line 92—92 thereof.
Figure 98:
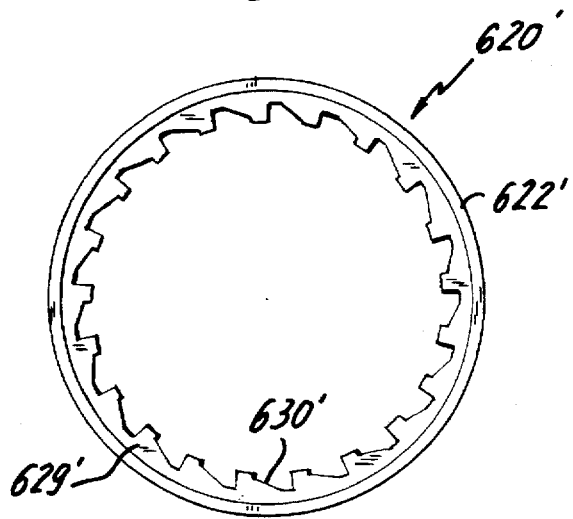
FIG. 98 is a top plan view of the intermittent counter ring according to another embodiment of the metered powder dose dispenser of FIG. 1.

A plurality of numerical indicia 628 are printed on the smooth combined outer surface of disc 622 and lower annular lip 624. Specifically, numbers "01" through "20" are printed equiangularly thereabout. Only one such number is shown in FIG. 74. It will be appreciated, however, that counting indicia other than numerical indicia 628 can be used, such as color designations, shape designations, Roman numerals, days of the week, and the like.

Twenty gear teeth 630 are equiangularly formed on the inner surface of disc 622 in correspondence with the twenty numbers of numerical indicia 628. All gear teeth 630 have the same depth in the radial direction. When intermittent counter ring 620 is seated on continuous counter ring 590, second rotation prevention spring detent 232 of base 200 engages with one gear teeth 630 at a time, to prevent clockwise rotation of intermittent counter ring 620 on base 200. As will be appreciated from the discussion which follows, gear teeth 630 extend along a larger diameter circle than gear teeth 602, so that gear teeth 630 are outwardly displaced in the radial direction from gear teeth 602.

Further, a dose limiting tab 632 extends upwardly from the upper surface of disc 622, corresponding to a position between numbers "01" and "20", to prevent operation of metered powder dose dispenser 10 after a prescribed number of doses have been dispensed. For example, where metered powder dose dispenser 10 is limited to dispensing 200 doses, dose limiting tab 632 will abut against dosage limiter tab 336 of adapter 320 after dispensing of the two hundredth dose, to prevent further relative rotation of powder housing 20 with respect to metering dose plate 180, as will be described with respect to the operation hereinafter.

Initially, number "20" of indicia 628 is aligned with number "0" of indicia 600 to form the number 200, which is exposed through transparent plastic window 330 of adapter 320. After the first dose is dispensed, both continuous counter ring 590 and intermittent counter ring 620 rotate together to expose the numbers "19" and "9", respectively, to form the number "199" which is exposed through window 330. After the next nine doses, only continuous counter ring 590 rotates one increment at a time for each dose. After the number "190" is exposed through window 330, the next dose results in both continuous counter ring 590 and intermittent counter ring 620 rotating to form the number "189". This operation continuous until the number "00" is exposed through window 330. At this time, intermittent counter ring 620 has been rotated to a position so that dose limiting tab 632 abuts against dosage limiter tab 336 of adapter 320, to prevent further relative rotation of powder housing 20 with respect to metering dose plate 180.

In order to cause such rotation of continuous counter ring 590 and intermittent counter ring 620, spring-biased pawl assembly 640 includes a pawl driver 642, as shown in FIGS.

3, 4 and 75–79. Pawl driver 642 includes an arcuate wall 644 having inwardly extending inturned flanges 646 and 648 at opposite side edges thereof. Arcuate wall 644 has a height greater than the combined height of continuous counter ring 590 and intermittent counter ring 620. A U-shaped retainer 650 is connected to the free ends of inturned flanges 646 and 648. U-shaped retainer 650 has a height less than that of arcuate wall 644. Accordingly, a loop defining an open area 652, is formed by arcuate wall 644, flanges 646 and 648 and U-shaped retainer 650.

A pawl 654 is formed on the outer or convex surface of arcuate wall 644. Thus, when pawl driver 642 is inserted on circular top wall 202 of base 200 in surrounding relation to cylindrical boss 216, pawl 654 can be inserted within a gear tooth 602. However, because gear teeth 630 extend along a larger diameter circle than gear teeth 602, pawl 654 can only engage with gear teeth 602 and not with gear teeth 630. The only exception is when pawl 654 engages within one of gear teeth 604 or 606. In such case, because gear teeth 604 and 606 are deeper than the remaining gear teeth 602, pawl 654 can reach into and engage with gear teeth 630. Since gear teeth 604 and 606 are spaced apart by ten gear teeth, pawl 654 engages within one of the gear teeth 604 or 606 every tenth dose dispensing, and thereby engages within one of gear teeth 630 at such time to rotatably drive intermittent counter ring 620 with continuous counter ring 590.

In order to bias pawl 654 into engagement with gear teeth 602, two spaced-apart L-shaped holders 656 are formed at the upper end of the concave or inner surface of arcuate wall 644. A flat spring 658 is bent into a checkmark configuration, with the free end of the larger length portion 660 being frictionally retained within L-shaped holders 656, while the free end of the short length portion 662 pushes against cylindrical boss 216 of base 220, thereby biasing pawl assembly 640 outwardly in the radial direction. This causes pawl 654 to enter into engagement with gear teeth 602.

As an alternative to the combination of pawl assembly 640 and flat spring 658, the pawl assembly can be fabricated from a somewhat resilient plastic material to have an appendage extending downward at an oblique angle, this appendage acting as a spring to bias the pawl assembly against cylindrical boss 216 as described above.

The operation of counter mechanism 580 will be described with respect to the schematic views of FIGS. 80–82. Lower spring retainer 260 rotates with reservoir body 22 180° relative to metering dose plate 180 between the stored position when closure cap 520 is threaded onto adapter 320 and the inhalation position when closure cap 520 is removed from adapter 320. FIG. 80 shows the relative position between arcuate pawl driving wall 274 of lower spring retainer 260, continuous counter ring 590, intermittent counter ring 620 and pawl assembly 640, when metered powder dose dispenser 10 is in the stored position. In such position, pawl 654 is engaged within a shallow gear tooth 602 of continuous counter ring 590, and therefore, does not engage with a gear tooth 630. Further, in such position, pawl driving end 276 of arcuate pawl driving wall 274 engages with pawl assembly 640.

When reservoir body 22 is rotated the first 178° toward the inhalation position, pawl driving end 278 of arcuate pawl driving wall 274 is rotated into engaged with the opposite side of pawl assembly 640, as shown in FIG. 81. As a result, as shown in FIG. 81, pawl 654 is rotated in the clockwise direction of FIG. 81, whereby pawl 654 rides out of the shallow gear tooth 602, thereby compressing spring 658. Continued rotation to the full 180°, as shown in FIG. 82, causes pawl 654 to rotate a slight amount and fall into the next gear tooth 604, which is a deep gear tooth, for example. Specifically, when pawl 654 moves from the position of FIG. 81 to the position of FIG. 82, spring 658 biases pawl 654 into gear tooth 604. Since gear tooth 604 is a deep gear tooth, pawl 654 also enters one of the gear teeth 630. At this point, metered powder dose dispenser 10 is in the inhalation position in which metered dose hole 184 is in alignment with venturi conduit 64.

After the user inhales the dose of powder 62, closure cap 520 is threaded back onto adapter 320. As a result, reservoir body 22 rotates back to its initial position of FIG. 80, which also results in rotation of lower spring retainer 260. During this rotation back 180°, that is, in the counterclockwise direction of FIG. 80, pawl driving end 276 of arcuate pawl driving wall 274 engages with pawl assembly 640 at the end of its movement to rotate pawl assembly 640 in the counterclockwise direction of FIG. 80 to its initial position. During such movement, since pawl 654 is engaged within deep gear tooth 604 and one of the gear teeth 630, both continuous counter ring 590 and intermittent counter ring 620 are rotated together one increment. In the case where pawl 654 is not engaged with one of the deep gear teeth 604 or 606, pawl does not engage with a gear tooth 630, so that only the continuous counter ring 590 would be rotated.

It will be appreciated that continuous counter ring 590 and intermittent counter ring 620 cannot rotate in the clockwise direction of FIGS. 80–82 because of first and second rotation prevention spring detents 224 and 232 which engage with gear teeth 602 and 630, respectively.

It will be appreciated that various changes can be made to the scope of the present invention. For example, rotation of metering dose plate 180 need not be 180°, but could be for a lesser or greater arcuate distance. In such case, the length of arcuate pawl driving wall 274 would be changed to incrementally drive pawl assembly 640.

Accordingly, with the present invention, a metered powder dose dispenser 10 is provided that accurately measures the doses of powdered medicament to be delivered to the patient. Specifically, dispenser 10 is greatly simplified in construction and assembly over the prior art.

All of the above elements, with the exception of springs 290 and 658, are preferably fabricated from readily available plastics, while the springs are preferably fabricated from suitable metals. Typically, the various components which do not require porosity or other special properties will be molded from one or more thermoplastic substances having the desired rigidity and strength. In some embodiments, the component containing the powder receptacle is relatively thin and, to maintain a required degree of surface flatness, will be constructed from a less easily deformed substance such as a reinforced plastic, ceramic or metal. Of course, materials selected must be chemically compatible with the medication to be dispensed. For reasons of cost, a maximum utilization of plastics will be preferred where the device is intended to be disposable with no, or only a limited number of, medicament refills after the initial charge has been dispensed.

A presently preferred embodiment of reservoir plug 90 comprises a thin, circular plate of electropolished stainless steel, which is insert molded onto a plastic base material. The metal portion contacts dosing plate 180 in the assembled device, providing a very flat, smooth and rigid surface to prevent powder leakage from the reservoir. In addition, the metal dissipates any static electricity charges generated by friction between surfaces during dose loading operations, which charges can adversely affect powder flow into and out of the dosing station. Other "composite" components can be used elsewhere in the device where special properties are required.

In order to assemble metered powder dose dispenser 10, powder housing 20 is first assembled. Specifically, reservoir plug 90 is inserted within reservoir body 22, flat spring 658 is inserted within L-shaped holders 656 of pawl assembly 640, desiccant holder 560 is snapped into closure cap 520, swirl nozzle 380 is assembled with driving body 120 and mouthpiece 440 is assembled with swirl nozzle 380. Next, continuous counter ring 590 is fit onto base 200 and intermittent counter ring 620 is fit onto continuous counter ring 590. Both counter rings 590 and 620 are rotated until the number "10" of intermittent counter ring 620 and the number "0" of continuous counter ring 590 are in alignment with small slot 214 of base 200. In other words, this corresponds to the number "100", and is directly opposite the number "200" which will be displayed through window 330 of adapter 320.

Pawl assembly 640 with spring 658 therein, is then positioned on top circular wall 202 of base 200 in surrounding relation to cylindrical boss 216, with pawl 654 being biased into engagement with gear tooth 604 in alignment with the number "1" and the gear tooth 630 in alignment with the number "11", that is, in alignment with the number "111". It will be appreciated that first and second rotation prevention spring detents 224 and 232 are in alignment with gear tooth 606 corresponding to number "1" and with the gear tooth 630 corresponding to the opposite number "11".

Thereafter, lower spring retainer 260 is positioned on boss 216 in surrounding relation to retaining post 218, with narrow driven ear 270 in alignment with the number "100" on rings 590 and 620. In such case, pawl driving end 276 thereof is in abutment with inwardly extending inturned flange 648 of pawl assembly 640. Coil spring 290 is then seated on disc 262 of lower spring retainer 260, and support plate 300 is placed on top of coil spring 290, with narrow driven ear 306 thereof in alignment with narrow driven ear 270 of lower spring retainer 260. Then, annular mounting post 188 of metering dose plate 180 is positioned through central circular hole 310 of support plate 300 and over retaining post 218 of base 200, with flats 190 and 222 in alignment. In such case, metered dose hole 184 is in alignment with radially extending slot 312 of support plate 300.

Then, reservoir body 22, having reservoir plug 90 assembled therewith, is inserted over metering dose plate 180, support plate 300, coil spring 290 and lower support plate 260, such that narrow driven ears 270 and 306 fit within narrow drive slot 34, and wider driven ears 272 and 308 fit within wider drive slot 36 of reservoir body 22. In such case, venturi conduit 64 is in alignment with metered dose hole 184. In order to assemble the above parts together, adapter 320 is then placed over the above assembly such that bridge 326 thereof is in alignment with small slot 214 of base 200. Adapter 320 is then pressed down until annular ledge 210 of base 200 snaps into annular groove 324 of adapter 320. At this time, coil spring 290 is compressed, the number "200" appears through window 330 of adapter 320, and recesses 340 and 342 of adapter 320 are in alignment with drive slots 34 and 36, respectively, of reservoir body 22.

Thereafter, powder supply conduit 60 is filled through the upper open end thereof. Then, driving body 120, with nozzle 380 and mouthpiece 440 thereon, is fit over reservoir body 22, such that circular plug conduit 144 of driving body 120 plugs the upper open end of powder supply conduit 60 and such that the upper open end of venturi conduit 64 extends through circular opening 142 in driving body 120. In this position, the lower edge of lower annular skirt section 128 of driving body 120 is positioned immediately above the upper edge of upper annular wall 332 of adapter 320.

Closure cap 520 is then threaded onto adapter 320, whereby powder housing 20 is rotated 180° relative to metering dose plate 180 so as to prime metered powder dose dispenser 10, that is, so as to scrape powder 62 into metered dose hole 184. This moves pawl 654 to the next gear tooth 602, as shown in FIG. 82.

When a user desires to inhale a dosage of the powder 62, closure cap 520 is unthreaded and removed, thereby rotating powder housing 20 back 180° so as to align venturi conduit 64 with metered dose hole 184, ready for inhalation. At this time, pawl 654 is rotated one increment back to the position shown in FIG. 80, whereby the next number "199" is displayed through window 330. When all 200 doses have been used, dose limiting tab 632 of intermittent counter ring 620 abuts against dosage limiter tab 336 of adapter 320 to prevent further rotation for dispensing. Accordingly, the numbers will not continue from "00" to "200".

Referring now to FIGS. 83–105, there is shown an alternative embodiment of a counter mechanism 580' for counting the number of doses that have been dispensed or indicating the number of doses that remain to be dispensed so as to warn the user of impending powder depletion, in which elements corresponding to counter mechanism 580 are identified by the same reference numerals with a prime thereafter. As with counter mechanism 580, it is preferable that counter mechanism 580' is a decrementing counter that indicates the number of doses that remain to be dispensed.

Basically, as part of the counter mechanism 580', the parts that have been modified are base 200', lower spring retainer 260', continuous counter ring 590', intermittent counter ring 620' and spring biased pawl assembly 640'.

In the first place, base 200' includes a circular top wall 202' having an annular skirt 204' extending downwardly from the periphery thereof. The peripheral edge of circular top wall 202' is cut-away to define an outer annular ledge 206'. An annular supporting lip 208' is formed on the outer surface of annular skirt 204' at the lower end thereof, so as to extend outwardly therefrom in the radial direction of annular skirt 204'. In addition, an annular retaining rim 210' is formed on the outer surface of annular skirt 204', parallel to supporting lip 208' and spaced thereabove, so as to extend outwardly from annular skirt 204' in the radial direction thereof. Retaining rim 210' has a diameter less than the diameter of supporting lip 208'. Thus, an annular retaining gap 212' is formed between supporting lip 208' and retaining rim 210'. It will be appreciated that, rather than retaining rim 210' being cut away along a very small arcuate distance to define a small slot therein, as in slot 214 of base 200, a small slot 214' is formed in supporting lip 208' for the same purpose. In addition, retaining rim 210' has a frusto-conical upper annular surface.

A cylindrical boss 216' is formed centrally and axially on the upper surface of circular top wall 202', and a coaxial retaining post 218' of lesser diameter than cylindrical boss 216' is formed at the upper end of cylindrical boss 216'. Accordingly, an outer annular ledge 220' is formed at the upper edge of cylindrical boss 216'. Retaining post 218' has an outer diameter slightly less than the inner diameter of annular mounting post 188 of metering dose plate 180. Retaining post 218' is formed with a slot 222' along the length thereof. In such case, mounting post 188 has a corresponding pin projection (not shown). Accordingly, due to the pin projection and slot 222', mounting post 188 of metering dose plate 180 is retained on retaining post 218' in a non-rotatable manner to ensure that metering dose plate 180 will remain stationary with respect to powder housing 20 when powder housing 20, which includes reservoir body 22, reservoir plug 90 and driving cap 120, is rotated.

As part of the counter mechanism, a first rotation prevention spring detent 224' is mounted in a cantilever manner on circular top wall 202'. Specifically, a curved vertical detent supporting wall 226' extends upwardly from circular top wall 202' such that the upper edge of spring detent 224' is substantially coplanar with the upper edge of cylindrical boss 216', and first rotation prevention spring detent 224' extends from one edge 228' of detent supporting wall 226', parallel to and spaced above circular top wall 202'. Further, the free end of first rotation prevention spring detent 224' is provided with a bevel 230' thereat which is oriented in the radial direction of circular top wall 202'.

A second rotation prevention spring detent 232' is mounted in a cantilever manner on circular top wall 202'. Specifically, second rotation prevention spring detent 232' extends from edge 228' of detent supporting wall 226', parallel to and spaced below first rotation prevention spring detent 224' and between first rotation prevention spring detent 224' and circular top wall 202'. The free end of second rotation prevention spring detent 232' is provided with an end 234' thereat having an increased thickness of a particular configuration, as will be explained hereinafter.

A sectored recess 236' is formed in circular top wall 202' in correspondence with detents 224' and 232'. Specifically, recess 236' includes a first radial boundary 238' substantially in line with the free end of detent 232', a second radial boundary 240 substantially in line with the connected end of detent 232', and a third boundary 242' connected between the inner ends of radial boundaries 238' and 240' and extending in alignment with the lengthwise direction of detent 232'.

In addition, a dosage limiting wall 243' is provided on the upper surface of top wall 202', extending from an edge of detent supporting wall 226' radially outwardly to the peripheral edge of top wall 202'. Dosage limiting wall 243' provides the same function as dosage limiter tab 336 of the first embodiment which is formed on the inner surfaces of connecting section 334 and lower annular wall 322. Dosage limiter tab 243' thereby prevents operation of the metered powder dose dispenser after a prescribed number of doses, for example, 200, have been dispensed, as will be understood from the explanation hereinafter.

As shown in FIGS. 88–92, spring retainer 260', which is mounted on annular ledge 220', over retaining post 218', includes a disc 262' having a central opening 264' sized to receive retaining post 218'. An annular boss 266' extends from the lower surface of disc 262' in surrounding relation to central opening 264'. When retaining post 218' extends through annular boss 266' and central opening 264', the lower edge of annular boss 266' seats upon annular ledge 220'.

An upper annular retaining lip 268' extends upwardly from the peripheral edge of disc 262'. Further, two radially extending driven ears 270' and 272' are formed in diametrically opposite positions at the peripheral edge of annular lip 268'. Ear 270' has a width substantially equal to the width of drive slot 34 of reservoir body 22 so as to fit therein and be driven thereby, and ear 272' has a width substantially equal to the width of drive slot 36 of reservoir body 22 so as to fit therein and be driven thereby.

Further, an arcuate pawl driving wall 274' extends from the lower surface of disc 262' between annular boss 266' and the periphery of disc 262'. Opposite ends of arcuate pawl driving wall 274' terminate in radially extending pawl driving end walls 276' and 278', each of which extends radially between annular boss 266' and the respective end of arcuate pawl driving wall 274', although pawl driving end wall 278' extends radially outwardly slightly past the end of arcuate pawl driving wall 274', the reason for which will be explained hereinafter. The arcuate distance between pawl driving end walls 276' and 278' is approximately 190°.

As shown in FIGS. 93–97, continuous counter ring 590' is formed by a disc 592' having a wall with a substantially rectangular cross-section. An outer annular ledge 594' is formed on the outer, lower edge of disc 592' by cutting away disc 592' thereat.

A plurality of numerical indicia 600' are printed on the smooth outer surface of disc 592'. Specifically, two successive sets of numbers "0" through "9" are printed equiangularly thereabout. It will be appreciated, however, that counting indicia other than numerical indicia 600', can be used, such as color designations, shape designations, Roman numerals, days of the week, and the like.

Twenty gear teeth 602' are equiangularly formed on the inner surface of disc 592' in correspondence with the twenty numbers of numerical indicia 600'. All gear teeth 602' have the same depth in the radial direction, with the exception that diametrically opposite gear teeth 604' and 606' of gear teeth 602', corresponding to a position between numbers "4" and "5" of numerical indicia 600', are deeper than the remaining gear teeth 602', that is, gear teeth 604' and 606' extend outwardly in the radial direction to a greater extent than the remaining gear teeth 602'. When continuous counter ring 590' is correctly positioned in the apparatus as will be explained hereinafter, first rotation prevention spring detent 224' of base 200' engages with one gear tooth. 602' at a time, to prevent clockwise rotation of continuous counter ring 590' on base 200'.

As shown in FIGS. 98–101, intermittent counter ring 620' is formed by a disc 622' having a wall with a substantially rectangular cross-section.

Figure 101:
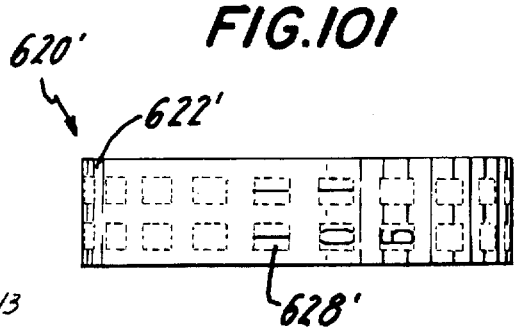
FIG. 101 is a side elevational view of the intermittent counter ring of FIG. 98.

A plurality of numerical indicia 628' are printed on the smooth outer surface of disc 622'. Specifically, numbers "0" through "20" are printed equiangularly thereabout. Only a few such numbers are shown in FIG. 101. It will be appreciated, however, that counting indicia other than numerical indicia 628' can be used, such as color designations, shape designations, Roman numerals, days of the week, and the like, may be used.

Figure 100:
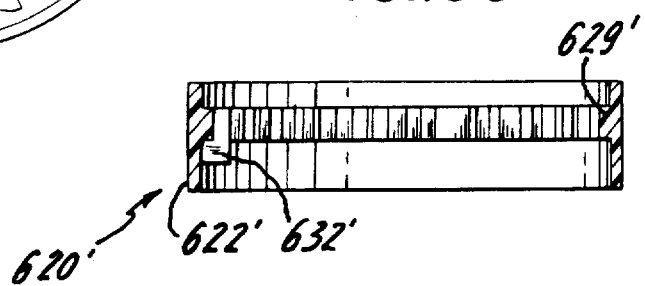
FIG. 100 is a cross-sectional view of the intermittent counter ring of FIG. 98, taken along line 100—100 thereof.
Figure 99:
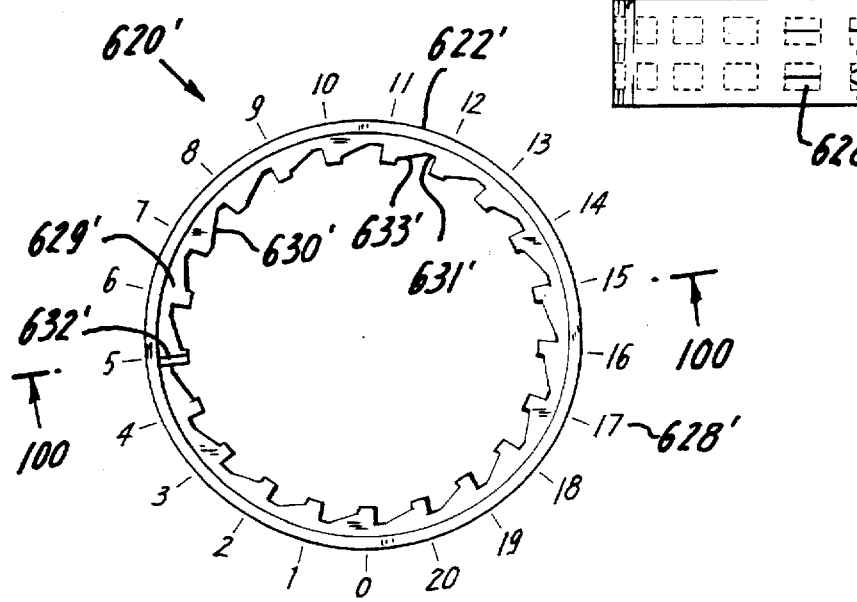
FIG. 99 is a bottom plan view of the intermittent counter ring of FIG. 98.

An inner annular wall 629' is provided on the inner surface of disc 622' at a position approximately two-thirds of the height of disc 622', as shown in FIG. 100. Twenty gear teeth 630' are equiangularly formed on the inner surface of inner annular wall 629' in correspondence with the twenty numbers of numerical indicia 628'. All gear teeth 630' have the same depth in the radial direction. It will be appreciated that each tooth 630' has an outer, substantially circumferentially extending portion 631' and a sloped portion 633' extending inwardly from outer, substantially circumferentially extending portion 631'. Because of circumferentially extending portion 631', the circumferential length of the sloped portion 633' is reduced and thereby made steeper than in the first embodiment of gear teeth 630. In this regard, free end 234' of second rotation prevention spring detent 232' of base 200', which has an increased thickness, has a configuration corresponding to that of gear teeth 630'. As a result of the circumferentially extending portion 631' and the increased slope of sloped portion 633', there is a greater torque that is necessary to move intermittent counter ring 620'. The reason for this arrangement is to prevent undesirable movement of intermittent counter ring 620' due to frictional forces with continuous counter ring 590', when it is desired that only continuous counter ring 590' should rotate.

With this arrangement, intermittent counter ring 620' is seated on base 200', and in particular, the lower edge of disc 622' seats upon annular ledge 206' of base 200' in surrounding relation to circular top wall 202'. When intermittent counter ring 620' is so seated, second rotation prevention spring detent 232' of base 200' engages with one gear tooth 630' at a time, to prevent clockwise rotation of intermittent counter ring 620' on base 200'. As will be appreciated from the discussion which follows, gear teeth 630' extend along a larger diameter circle than gear teeth 602', so that gear teeth 630' are outwardly displaced in the radial direction from gear teeth 602'.

Further, continuous counter ring 590' is rotatably seated on intermittent counter ring 620', and in particular, outer annular ledge 594' seats on the upper edge of disc 622' for rotation relative thereto. It will be appreciated that this is the reverse of the first-mentioned embodiment in which intermittent counter ring 620 sits on continuous counter ring 590.

Further, a dose limiting tab 632' extends downwardly from the lower surface of inner annular wall 629', corresponding to a position at the number "05", to prevent operation of metered powder dose dispenser after a prescribed number of doses have been dispensed. For example, where metered powder dose dispenser 10 is limited to dispensing 200 doses, dose limiting tab 632' will abut against dosage limiting wall 243' of base 200', after dispensing of the two hundredth dose, to prevent further relative rotation of powder housing 20 with respect to metering dose plate 180.

Initially, number "20" of indicia 628' is aligned with number "0" of indicia 600' to form the number "200", which is exposed through transparent plastic window 330 of adapter 320. After the first dose is dispensed, both continuous counter ring 590' and intermittent counter ring 620' rotate together to expose the numbers "19" and "9", respectively, to form the number "199" which is exposed through window 330. After the next nine doses, only continuous counter ring 590' rotates one increment at a time for each dose. After the number "190" is exposed through window 330, the next dose results in both continuous counter ring 590' and intermittent counter ring 620' rotating to form the number "189". This operation continues until the number "00" is exposed through window 330. At this time, intermittent counter ring 620' has been rotated to a position so that dose limiting tab 632' abuts against dosage limiting wall 243' of base 200', to prevent further relative rotation of powder housing 20 with respect to metering dose plate 180.

Figure 103:
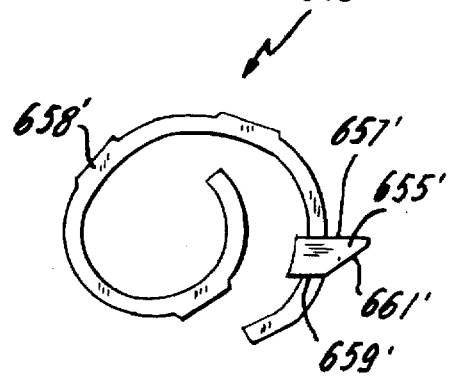
FIG. 103 is a top plan view of the pawl assembly of FIG. 102.
Figure 104:
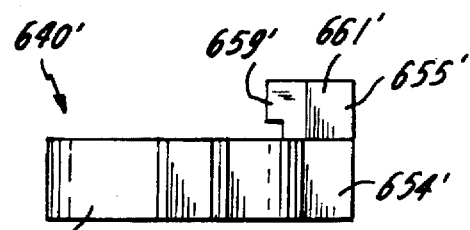
FIG. 104 is a side elevational view of the pawl assembly of FIG. 102.
Figure 102:
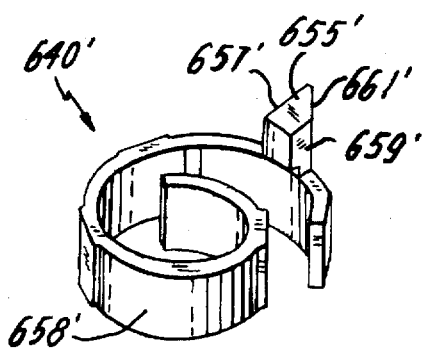
FIG. 102 is a perspective view of the pawl assembly according to another embodiment of the metered powder dose dispenser of FIG. 1.

In order to cause such rotation of continuous counter ring 590' and intermittent counter ring 620', spring-biased pawl assembly 640' includes a pawl 654' having a substantially triangular configuration, secured near one end of a flat, plastic spiral spring 658', as shown in FIGS. 102–104. Pawl 654' has a height equal to the height of spring 658'. In addition, a pawl extension 655' of the same configuration as pawl 654' is mounted on top of pawl 654' so as to extend above spring 658'. Pawl extension 655' has a long radial face 657' and a substantially parallel short radial face 659', with short radial face 659' terminating in an angled face 661' that is connected to the end of long radial face 657'.

Figure 105:
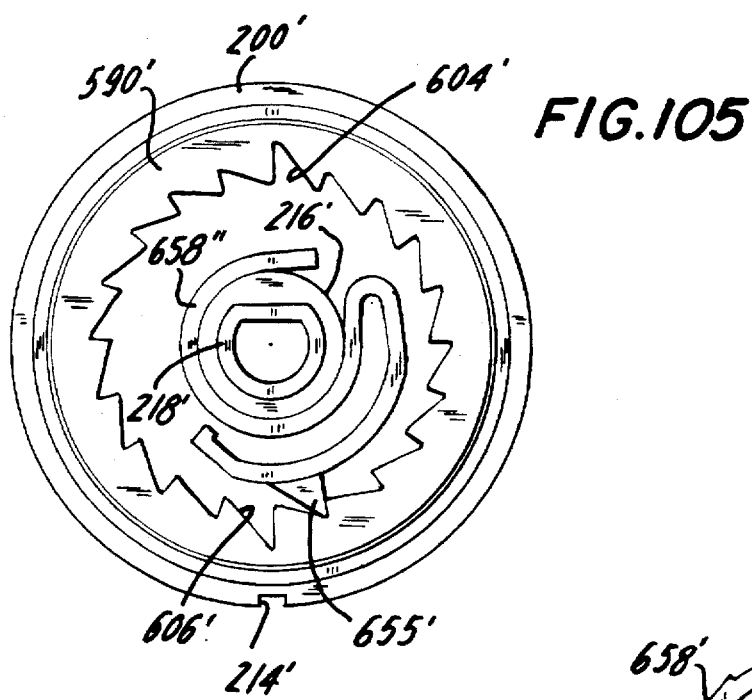
FIG. 105 is a top plan view of a pawl assembly having an S-shaped spring according to another embodiment of the present invention, in which the pawl assembly is assembled with the base and the counter rings, but with the spring detents on the base omitted.

As an alternative, as shown in FIG. 105, an S-shaped spring 658" can be used in place of spiral spring 658". In FIG. 105, spring detents 224' and 232' have been omitted for the sake of clarity.

When pawl assembly 640' is inserted on circular top wall 202' of base 200' in surrounding relation to cylindrical boss 216', pawl extension 655' is biased by spring 658' within a gear tooth 602'. However, because gear teeth 630' extend along a larger diameter circle than gear teeth 602', pawl 654' does not engage with gear teeth 630' at this time. The only exception is when pawl extension 655' engages within one of gear teeth 604' or 606'. In such case, because gear teeth 604' and 606' are deeper than the remaining gear teeth 602', pawl 654' can reach into and engage with gear teeth 630'. Since gear teeth 604' and 606' are spaced apart by ten gear teeth, pawl extension 655' engages within one of the gear teeth 604' or 606' every tenth dose dispensing, and thereby pawl 654' engages within one of gear teeth 630' at such time to rotatably drive intermittent counter ring 620' with continuous counter ring 590'.

The operation of counter mechanism 580' will now be described. Lower spring retainer 260' rotates with reservoir body 22 relative to metering dose plate 180 between the stored position when closure cap 520 is threaded onto adapter 320 and the inhalation position when closure cap 520 is removed from adapter 320.

In the initial position, the number "20" of intermittent counter ring 620' and the number "0" of continuous counter ring 590' are positioned at transparent plastic window 330, so as to display a combined number "200" corresponding to the number of doses remaining. Window 330 is positioned diametrically opposite small slot 214' on base 200'. Also, pawl extension 655' is positioned 90° counterclockwise from slot 214', so that pawl extension 655' is engaged within a deep gear tooth 604' and pawl 654' is engaged within a gear tooth 630'. Further, pawl driving end wall 278' abuts against long radial face 657'. In this position, driven ear 270' is substantially in line with slot 214'.

When reservoir body 22 is rotated from the closed to the open operative position, pawl driving end wall 276' of lower spring retainer 260' is rotated into engagement with short radial face 659' of pawl extension 655'. In this position, driven ear 272' is substantially in line with slot 214' As a result, pawl 654' and pawl extension 655' are rotated in the counterclockwise direction. During such movement, since pawl extension 655' and pawl 654' are engaged within deep gear tooth 604' and one of the gear teeth 630', respectively, both continuous counter ring 590' and intermittent counter ring 620' are rotated together one increment. Accordingly, the number "19" of intermittent counter ring 620' and the number "9" of continuous counter ring 590' are positioned at transparent plastic window 330, so as to display a combined number "199" corresponding to the number of doses remaining. At this point, metered powder dose dispenser 10 is in the inhalation position in which metered dose hole 184 is in alignment with venturi conduit 64.

After the user inhales the dose of powder 62, closure cap 520 is threaded back onto adapter 320. As a result, reservoir body 22 rotates back to its initial position, which also results in rotation of lower spring retainer 260' in the clockwise direction. During this rotation back, pawl driving end wall 278' of lower spring retainer 260' is rotated into engagement with long radial face 657' of pawl extension 655'. As a result, pawl 654' and pawl extension 655' are rotated in the counterclockwise direction, during which time, pawl extension 655' rides out of the gear tooth 604' and pawl 654' rides out of the gear tooth 630', thereby compressing spring 658'. Continued rotation causes pawl extension 655' to rotate a slight amount and fall into the next gear tooth 602', which is a shallow gear tooth, for example. Specifically, spring 658' biases pawl extension 655' into a shallow gear tooth 602'.

Since gear tooth 602' is a shallow gear tooth, pawl 654' does not enter one of the gear teeth 630'. At this position, pawl driving end wall 278' abuts against long radial face 659' and driven ear 270' is substantially in line with slot 214'.

It will be appreciated that during the movement of pawl extension 654' from one gear tooth 602' to another gear tooth 602', pawl extension 654' rides against pawl driving end wall 278'. The reason that pawl driving end wall 278' extends radially outward past arcuate pawl driving wall 274' is to prevent pawl 654' from moving past pawl driving end wall 278' into alignment with arcuate pawl driving wall 274', since this would otherwise prevent compression of spring 658' and thereby prevent pawl extension 655' from moving from one tooth 602' to another tooth 602'.

This operation is continued for each dose. In the case where pawl extension 655' is not engaged with one of the deep gear teeth 604' or 606', pawl 654' does not engage with a gear tooth 630', so that only the continuous counter ring 590' would be rotated.

It will be appreciated that continuous counter ring 590' and intermittent counter ring 620' cannot rotate in the clockwise direction because of first and second rotation prevention spring detents 224' and 232' which engage with gear teeth 602' and 630', respectively.

Accordingly, with the present invention, a counter mechanism is provided which has a high counting capability of doses dispensed or remaining to be dispensed. Specifically, there are two separately rotatable counter rings, one for the ones digits of a counted number and the other for tens and hundreds digits for the counted number, with the counter rings being rotatable along the same common axis as the powder housing.

Further, a swirl nozzle is provided in which there is improved micronization of the powder and improved mixing of the micronized powder with suction air. Specifically, the powder first changes direction from an axial direction of the inhalation or venturi conduit to a transverse direction substantially perpendicular to the axial direction; continuously changes direction in a spiral manner in a swirl cavity extending in the transverse direction; and upon exiting the swirl cavity, changes direction back to the axial direction through a supply chimney, while retaining a swirl component of the flow.

Still further, with the present invention, the metered powder dose dispenser is automatically primed every time that the closure cap is threaded thereon and is automatically ready to use every time that the closure cap is threadedly removed. If multiple actuations are desired for the dose at a given time, the user is not required to repeatedly remove and replace the cap, but can simply perform the reciprocal rotation of either the upper or lower portions of the device while holding the other portion stationary, then replace the cap for storage until the next prescribed dose is due.

Having described specific preferred embodiments of the invention with reference to the accompanying drawings, it will be appreciated that the present invention is not limited to those precise embodiments and that various changes and modifications can be effected therein by one of ordinary skill in the art without departing from the scope or spirit of the invention as defined by the appended claims.

What is claimed is:

1. A counter for a powdered medication inhaler which is actuated for dose delivery by a reciprocating partial relative rotation of its components, said counter comprising:

a continuous counter ring having counting indicia thereon and having gear teeth therearound;

an intermittent counter ring adjacent to said continuous counter ring, said intermittent counter ring having counting indicia thereon and having gear teeth therearound;

display means through which one of said counting indicia from said continuous counter ring and one of said counting indicia from said intermittent counter ring are displayed to indicate a count corresponding to a number of doses of powdered material that have been dispensed or remain to be dispensed;

actuating means including pawl means engaging with said gear teeth of said continuous counter ring, and said intermittent counter ring, for rotating said continuous counter ring one increment each time that a dose of the powdered material is dispensed to display another one of said counting indicia of said continuous counter ring through said display means, and for rotating said intermittent counter ring one increment every predetermined number of rotational increments of said continuous counter ring to display another one of said counting indicia of said intermittent counter ring through said display means; and spring means for biasing said pawl means into engagement with said gear teeth of said continuous counter ring and said intermittent counter ring.

2. The counter according to claim 1, wherein said pawl means includes a pawl secured to the end of said spring means for engagement within the gear teeth of one of said continuous counter ring and said intermittent counter ring, and a pawl extension secured to the end of said spring means and positioned at a height above said pawl for engagement within the gear teeth of the other of said continuous counter ring and said intermittent counter ring.

3. The counter according to claim 1, wherein said gear teeth of said continuous counter ring are arranged in correspondence with said counting indicia thereon, and said gear teeth of said intermittent counter ring are arranged in correspondence with said counting indicia thereon.

4. The counter according to claim 1, wherein the gear teeth of said continuous counter ring include a plurality of successive first gear teeth of a first depth and at least one second gear tooth of a second, greater depth, each said second gear tooth being positioned after every predetermined number of said first gear teeth; and said intermittent counter ring includes a plurality of successive third gear teeth of a depth equal to the depth of each said second gear tooth of said continuous counter ring so that said pawl means engages with successive ones of said first gear teeth during successive dosing operations and engages with one said second gear tooth of said continuous counter ring and one said third gear tooth of said intermittent counter ring after a plurality of the dosing operations.

5. The counter according to claim 4, wherein said first and second gear teeth are formed on an inner surface of said continuous counter ring and said third gear teeth are formed on an inner surface of said intermittent counter ring.

6. The counter according to claim 1, wherein said pawl means engages said gear teeth of said continuous counter ring and said intermittent counter ring to rotate said continuous counter ring and said intermittent counter ring in a first rotational direction, and further including detent means for preventing rotation of said continuous counter ring and said intermittent counter ring in a second rotational direction opposite to said first rotational direction.

7. The counter according to claim 6, wherein said detent means includes first rotation prevention detent means mounted on said base for engaging with one of said first and second gear teeth to prevent rotation of said continuous counter ring in said second rotational direction and second rotation prevention detent means mounted on said base for engaging with one of said third gear teeth to prevent rotation of said intermittent counter ring in said second rotational direction.

8. The counter according to claim 1, further including pawl driver means for incrementally rotating said pawl means, said pawl driver means including a retainer rotatably mounted coaxially with said continuous counter ring and said intermittent counter ring, said retainer including first pawl driver means for engaging with one side of said pawl means to incrementally rotate said pawl means in a first rotational direction at the end of rotation of said retainer in said first rotational direction to cause said pawl means to engage a successive gear tooth of said continuous counter ring, and second pawl driver means for engaging an opposite side of said pawl means to incrementally rotate said pawl means in a second, opposite rotational direction at the end of rotation of said retainer in said second, opposite rotational direction to cause said pawl means to incrementally rotate said continuous counter ring therewith.

9. The counter according to claim 8, wherein said first and second pawl driver means are formed as opposite edges of an arcuate pawl driving wall connected with said retainer.

10. The counter according to claim 8, wherein said first and second pawl driver means are formed as radially extending pawl driving end walls connected with said retainer.

11. The counter according to claim 8, wherein said first and second pawl driver means are spaced apart by a distance such that rotation of said retainer by a first arcuate distance causes incremental rotation of said pawl means by a second smaller arcuate distance.

12. The counter according to claim 1, wherein the gear teeth of said intermittent counter ring have a configuration with an outer, substantially circumferentially extending portion and a sloped portion extending inwardly from said circumferentially extending portion.

13. The counter according to claim 1, wherein said continuous counter ring is rotatably mounted, and said intermittent counter ring is rotatably mounted on said continuous counter ring coaxially with said continuous counter ring.

14. The counter according to claim 1, wherein said intermittent counter ring is rotatably mounted, and said continuous counter ring is rotatably mounted on said intermittent counter ring coaxially with said intermittent counter ring.

* * * * *